(12) United States Patent
Faget et al.

(10) Patent No.: US 9,376,493 B2
(45) Date of Patent: Jun. 28, 2016

(54) ANTIBODIES DIRECTED AGAINST ICOS AND USES THEREOF

(75) Inventors: Julien Faget, Lyons (FR); Christophe Caux, Lyons (FR); Christine Menetrier-Caux, Lyons (FR); Jacques Nunes, Marseilles (FR); Daniel Olive, Marseilles (FR)

(73) Assignees: INSERM (Institut National de la Sante et de la Recherche Mediacale), Paris (FR); INSTITUT JEAN PAOLI & IRENE CALMETTES, Marseilles (FR); UNIVERSITE D'AIX-MARSEILLE, Marseilles (FR); UNIVERSITE CLAUDE BERNARD, Villeurbanne (FR); CENTRE LEON BERARD, Lyons (FR)

( * ) Notice: Subject to any disclaimer, the term of this patent is extended or adjusted under 35 U.S.C. 154(b) by 186 days.

(21) Appl. No.: 14/008,423

(22) PCT Filed: Mar. 29, 2012

(86) PCT No.: PCT/EP2012/055735
§ 371 (c)(1),
(2), (4) Date: Dec. 10, 2013

(87) PCT Pub. No.: WO2012/131004
PCT Pub. Date: Oct. 4, 2012

(65) Prior Publication Data
US 2014/0086923 A1   Mar. 27, 2014

(30) Foreign Application Priority Data

Mar. 31, 2011   (EP) .................................... 11305380

(51) Int. Cl.
*C07K 16/28* (2006.01)
*A61K 39/395* (2006.01)
*G01N 33/569* (2006.01)

(52) U.S. Cl.
CPC ............. *C07K 16/28* (2013.01); *C07K 16/2818* (2013.01); *G01N 33/56972* (2013.01); *C07K 2317/75* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 7,259,247 B1 * | 8/2007 | Kroczek | ............... 530/388.75 |
| 2004/0001831 A1 * | 1/2004 | Rottman et al. | .......... 424/146.1 |
| 2004/0146991 A1 | 7/2004 | Tsuji | |
| 2004/0180052 A1 | 9/2004 | Tsuji | |

FOREIGN PATENT DOCUMENTS

| | | |
|---|---|---|
| EP | 1125585 | 8/2001 |
| EP | 1374901 | 1/2004 |
| EP | 1374902 | 1/2004 |
| WO | 2008/137915 | 11/2008 |
| WO | 2010/056804 | 5/2010 |
| WO | 2011/041613 | 4/2011 |

OTHER PUBLICATIONS

Conti et al., Cent Eur J Immunol 2015; 40 (3): 380-386.*
Liappas et al., 2015; BioMed Research International, vol. 2015, Article ID 416480, 9 pages.*
Ochs et al., J Allergy Clin Immunol. May 2009; 123(5): 977-985.*
Botturi et al., "Differences in allergen-induced T cell activation between allergic asthma and rhinitis: Role of CD28, ICOS and CTLA-4," 12:25 (2011) XP002657740.
Deng et al., "An agonist human ICOS monoclonal antibody that induces T cell activation and inhibits proliferation of a myeloma cell line," Hybridoma and Hybridomics, 23(3):176-182 (2004).
Frey et al., "Inducible costimulator (ICOS) blockade inhibits accumulation of polyfunctional T helper 1/T helper 17 cells and mitigates autoimmune arthritis," Ann. Rheum. Dis., 69(8):1495-1501 (2010) XP008141861.
Guo et al., "Simultaneous blockade of co-stimulatory signals, CD28 and ICOS, induced a stable tolerance in rat heart transplantation," Transplant Immunol., 12(1):41-48 (2003) XP002657737.
International Search Report in PCT/EP2012/055735 dated Sep. 28, 2012.
Izawa et al., "A novel alloantigen-specific CD8+PD1+ regulatory T cell induced by ICOS-B7h blockade in vivo," J. Immunol., 179(2):786-796 (2007) XP002657739.
Katsumata et al., "Attenuation of experimental autoimmune myositis by blocking ICOS-ICOS ligand interaction," J. Immunol., 179(6):3772-3779 (2007) XP002657738.
Kawamoto et al., "Expression and function of inducible co-stimulator in patients with systemic lupus erythematosus: possible involvement in excessive interferon-gamma and anti-double-stranded DNA antibody production," Arth. Res. Ther., 8(3):R62.1-R62.14 (2006) XP002665547.
Peng et al., "Transient blockade of the inducible costimulator pathway generates long-term tolerance to factor VIII after nonviral gene transfer into hemophilia A mice," 112(5):1662-1672 (2008) XP055003460.
Nanji et al., "Multiple combination therapies involving blockade of ICOS/B7RP-1 costimulation facilitate long-term islet allograft survival," Am. J. Transplant, 4(4):526-536 (2004) XP002657736.

(Continued)

*Primary Examiner* — Ilia Ouspenski
(74) *Attorney, Agent, or Firm* — McAndrews, Held & Malloy, Ltd.

(57) ABSTRACT

The present invention provides antibodies directed against ICOS or a derivative thereof which neutralize ICOS engagement on Treg by inhibiting the fixation between ICOS and ICOS-L and abrogate proliferation of Treg induced by plasmacytoid dendritic cells. The present invention further provides antibodies directed against ICOS or a derivative thereof which induce IL-10 and IFNγ production, induce CD4+ T cells proliferation, reduce Tconv proliferation, and increase the immunosuppressive function of Treg.

4 Claims, 9 Drawing Sheets

(56) References Cited

OTHER PUBLICATIONS

Figure 1:
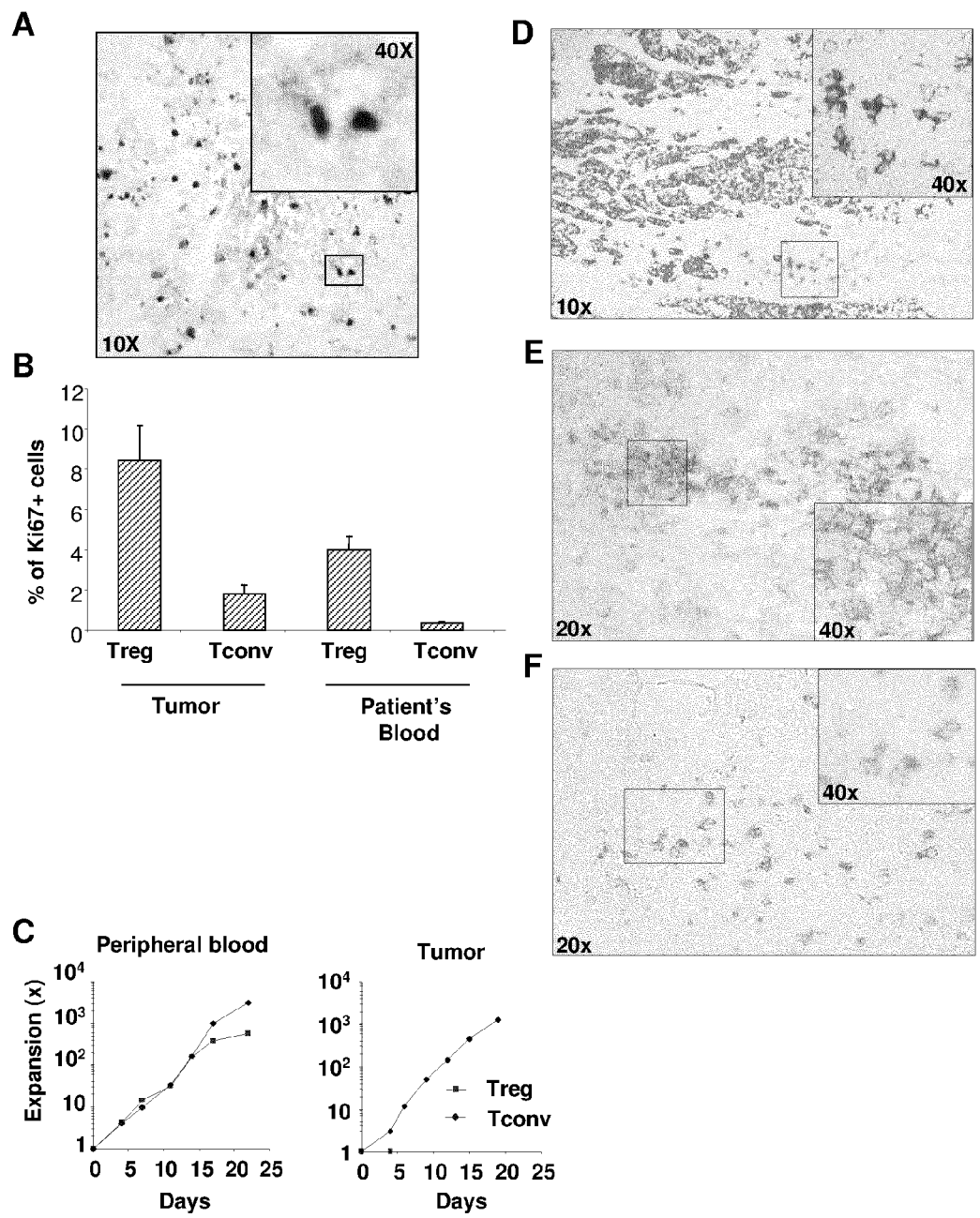

Rutitzky et al., "Disruption of the ICOS-B7RP-1 costimulatory pathway leads to enhanced hepatic immunopathology and increased gamma interferon production by CD4 T cells in murine schistosomiasis," Infect. Immun., 71 (7):4040-4044 (2003) XP002665550.

Totsuka et al., "Ameliorating effect of anti-inducible costimulator monoclonal antibody in a murine model of chronic colitis," Gastroenterology, 124(2):410-421 (2003) XP002297200.

Wiley et al., "Evaluation of inducible costimulator/B7-related protein-1 as a therapeutic target in a murine model of allergic airway inflammation," Am. J. Resp. Cell Mol. Biol., 28(6):722-730 (2003) XP002665546.

* cited by examiner

A

B

ANTIBODIES DIRECTED AGAINST ICOS AND USES THEREOF

The present application is filed pursuant to 35 U.S.C. 371 as a U.S. National Phase application of International Patent Application No. PCT/EP2012/055735, which was filed Mar. 29, 2012, claiming the benefit of priority to European Patent Application No. 11305380.5, which was filed on Mar. 31, 2011. The entire text of the aforementioned applications is incorporated herein by reference in its entirety.

FIELD OF THE INVENTION

The invention relates to antibodies directed against ICOS and uses thereof.

BACKGROUND OF THE INVENTION

In several cancers, the establishment of an immunosuppressive T cell response is correlated with a poor prognosis and disease progression.

Among the different cellular effectors involved in the establishment of immune tolerance, the $CD4^+$ regulatory T lymphocytes subset (Treg) is specialised in the suppression of the other T cell (Tconv) as well as dendritic function. Said suppression may be correlated with a poor survival rate of patient suffering from cancer, especially from breast cancer.

It has been shown that large amounts of IL-10 and low quantities of IFNγ produced by $CD4^+$ T cells are associated with reduced $CD8^+$ T cell cytotoxic capacity, lower T cells proliferation and participate to monocytes differentiation into immunosuppressive M2c type macrophages, related to the Tumor Associated Macrophage (TAM).

The inventors previously reported that memory $CD3^+$ $CD4^+$ T cells that encompass large amounts of Treg (Ta-Treg) infiltrated primary breast tumors. Primary breast tumor infiltration by Ta-Treg and plasmacytoid DC (pDC) are both associated with poor prognosis and poor survival of the patient suffering from breast tumors.

The inventors further confirmed that immunosuppressive mechanisms involving Treg are observed in most cancers and chronic infections. These suppressive mechanisms prevent an efficient immune response against cancer and chronic viral infection.

Currently Treg are targeted in cancers and chronic infections using cell therapy, anti-CD25 mAbs or low doses chemotherapy. However, said strategies did not provide acceptable results.

In addition, it has been reported that Treg might have an important role in diseases associated with or caused by an excessive immune response.

However, there is currently no available and efficient strategy for treating Treg associated diseases. There is still thus a great need for providing efficient therapeutic strategies targeting diseases involving Treg.

SUMMARY OF THE INVENTION

Surprisingly, the inventors have shown that the interaction between ICOS and its ligand plays a central role in the activation, proliferation and suppressive function of Treg in some cancers through interaction with plasmacytoid dendritic cells (pDC). They then concentrated their effort to generate specific antibodies with antagonist and agonist effects.

The antagonist antibodies are efficient for treating a disease or a condition associated with Treg mediated suppression of immune response. The agonist antibodies are efficient for treating a disease or a condition associated with or caused by an excessive immune response.

The present invention thus relates to an antibody directed against ICOS or a derivative thereof which:
  neutralizes ICOS engagement on Treg by inhibiting the fixation between ICOS and ICOS-L; and
  abrogates proliferation of Treg induced by pDC.
In the context of the present invention, said antibody may also be called "antagonist antibody".

The invention further relates to an antibody directed against ICOS, wherein said antibody is selected from the group consisting of Icos 145-1 and Icos 314-8, respectively obtainable from the hybridoma deposited at the "Collection Nationale de Cultures de Microorganismes" (CNCM, Institut Pasteur, 25 rue du Docteur Roux, 75724 Paris Cedex 15, France), in accordance with the terms of Budapest Treaty, on Jul. 2, 2009 under the accession numbers CNCM I-4179 and CNCM I-4180 and derivatives thereof.

The invention also relates to an antagonist antibody directed against ICOS according to the invention or a derivative thereof for use as a medicament. The invention further relates to an antagonist antibody directed against ICOS according to the invention or a derivative thereof for use for treating cancers or chronic infections.

The present invention further relates to an antibody directed against ICOS or a derivative thereof which:
  induces IL-10 and IFNγ production;
  induces CD4+ T cells proliferation;
  reduces Tconv proliferation, and
  increases the immunosuppressive function of Treg.
In the context of the present invention, said antibody may also be called "agonist antibody".

The invention also relates to an antibody directed against ICOS, wherein said antibody is selected from the group consisting of Icos 53-3, Icos 88-2 and Icos 92-17, respectively obtainable from the hybridoma deposited at the "Collection Nationale de Cultures de Microorganismes" (CNCM, Institut Pasteur, 25 rue du Docteur Roux, 75724 Paris Cedex 15, France), in accordance with the terms of Budapest Treaty, on Jul. 2, 2009 under the accession numbers CNCM I-4176, CNCM I-4177, CNCM I-4178 and derivatives thereof.

The invention relates to an agonist antibody according to the invention or a derivative thereof for use as a medicament. The invention also relates to an agonist antibody according to the invention or a derivative thereof for use for treating autoimmune diseases, transplantation rejection or a graft versus host disease.

DETAILED DESCRIPTION OF THE INVENTION

Definition

As used herein, the terms "ICOS" or "Inductible T cell costimulator" refer to a transmembrane homodimeric glycoprotein of 55 to 60 kDa which presents an IgV type domain in its extracellular part and a tyrosine within an YMFM motif in its cytoplasmic part. It has been shown that ICOS engagement with its ligand induces the phosphorylation of the tyrosine in the cytoplasmic part of ICOS. Said phosphorylation is responsible for the recruitment of the p85 PI3K regulatory subunit, which activates the PI3K/AKT signaling pathway.

ICOS engagement is also described to induce the expression of CD40L at the cell surface. CD40L is known to have an important effect in the cooperation between T lymphocytes and B lymphocytes.

ICOS has been found to be expressed, following TCR activation, on conventional T cells (Tconv CD4+, CD8+ subsets) as well as on Treg. The inventors showed that said activation was more important in patients suffering from melanoma or breast cancer.

As used herein, the terms "ICOSL", "ICOS-L" and "B7-H2" refer to an ICOS ligand. Said ligand is present on lymphoid cells such as B lymphocytes, macrophages, dendritic cells, as well as on non-lymphoid cells such as endothelial or epithelial cells. ICOS engagement has an important role in the lymphocyte activation, and it induces the proliferation and survival of T lymphocytes, especially Treg.

As used herein, the term "JICOS 1" refers to a specific cell line expressing ICOS.

As used herein, a "monoclonal antibody" in its various grammatical forms refers to a population of antibodies that contains only one species of antibody combining sites capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g. a bispecific monoclonal antibody. Although historically a monoclonal antibody was produced by immortalization of a clonally pure immunoglobulin secreting cell line, a monoclonally pure population of antibody molecules can also be prepared by the methods of the present invention. Laboratory methods for preparing monoclonal antibodies are well known in the art (see, for example, Harlow et al., 1988). Monoclonal antibodies (mAbs) may be prepared by immunizing purified mutated TXAS into a mammal, e.g. a mouse, rat, human and the like mammals. The antibody-producing cells in the immunized mammal are isolated and fused with myeloma or heteromyeloma cells to produce hybrid cells (hybridoma). The hybridoma cells producing the monoclonal antibodies are utilized as a source of the desired monoclonal antibody. This standard method of hybridoma culture is described in Kohler and Milstein (1975). While mAbs can be produced by hybridoma culture the invention is not to be so limited. Also contemplated is the use of mAbs produced by an expressing nucleic acid cloned from a hybridoma of this invention. That is, the nucleic acid expressing the molecules secreted by a hybridoma of this invention can be transferred into another cell line to produce a transformant. The transformant is genotypically distinct from the original hybridoma but is also capable of producing antibody molecules of this invention, including immunologically active fragments of whole antibody molecules, corresponding to those secreted by the hybridoma. See, for example, U.S. Pat. No. 4,642,334 to Reading; PCT Publication No.; European Patent Publications No. 0239400 to Winter et al. and No. 0125023 to Cabilly et al. Antibody generation techniques not involving immunisation are also contemplated such as for example using phage display technology to examine naive libraries (from non-immunised animals); see Barbas et al. (1992), and Waterhouse et al. (1993).

As used herein, the expression "anti-ICOS antibody" refers to a monoclonal antibody directed against ICOS, preferably obtained using recombinant ICOS-Fc as immunogen.

As used herein, the expression "derivative of an antibody" refers to an antibody which comprises the 6 CDRs of said antibody.

As used herein, the expression "53.3 mAb" or "Icos 53-3" refers to a monoclonal antibody directed against ICOS deposited at the CNCM on Jul. 2, 2009 under the accession number CNCN I-4176. Said antibody is an agonist of ICOS. The expression "a derivative of 53.3 mAb" refers to an anti-ICOS antibody which comprises the 6 CDRs of 53.3 mAb.

As used herein, the expression "88.2 mAb" or "Icos 88-2" refers to a monoclonal antibody directed against ICOS deposited at the CNCM on Jul. 2, 2009 under the accession number CNCN I-4177. Said antibody is an agonist of ICOS. The inventors have shown that use of said antibody in presence of IL-2 favors Treg proliferation and the IL-10 secretion. The expression "a derivative of 88.2 mAb" refers to an anti-ICOS antibody which comprises the 6 CDRs of 88.2 mAb.

The 6 CDRs of 88.2 mAb are as in Table 1 below:

TABLE 1

| | DNA sequence | Aminoacid sequence |
|---|---|---|
| H-CDR1 | GGCTACAGTTTCACCAGCTACTGG ATAAAC (SEQ ID NO: 17) | GYSFTSYWIN (SEQ ID NO: 23) |
| H-CDR2 | AATATTTATCCTTCTGATAGTTAT ACTAACTACAATCAAATGTTCAAG GAC (SEQ ID NO: 18) | NIYPSDSYTNYNQMFKD (SEQ ID NO: 24) |
| H-CDR3 | TGGAATCTTTCTTATTACTTCGAT AATAACTACTACTTGGACTAC (SEQ ID NO: 19) | WNLSYYFDNNYYLDY (SEQ ID NO: 25) |
| L-CDR1 | AGGTCTAGTAAGAGTCTCCTGCAT AGTAATGGCAACACTTACTTGTAT (SEQ ID NO: 20) | RSSKSLLHSNGNTYLY (SEQ ID NO: 26) |
| L-CDR2 | CGGATGTCCAACCTTGCCTCA (SEQ ID NO: 21) | RMSNLAS (SEQ ID NO: 27) |
| L-CDR3 | ATGCAACATCTAGAATATCCGTGG ACG (SEQ ID NO: 22) | MQHLEYPWT (SEQ ID NO: 28) |

As used herein, the expression "92.17 mAb" or "Icos 92-17" refers to a monoclonal antibody directed against ICOS deposited at the CNCM on Jul. 2, 2009 under the accession number CNCN I-4178. Said antibody is an agonist of ICOS. The expression "a derivative of 92.17 mAb" refers to an anti-ICOS antibody which comprises the 6 CDRs of 92.17 mAb.

As used herein, the expression "145.1 mAb" or "Icos 145-1" refers to a monoclonal antibody directed against ICOS deposited at the CNCM on Jul. 2, 2009 under the accession number CNCN I-4179. Said antibody is an antagonist of ICOS. The expression "a derivative of 145.1 mAb" refers to an anti-ICOS antibody which comprises the 6 CDRs of 145-1 mAb.

As used herein, the expression "314.8 mAb" or "Icos 314-8" refer to a monoclonal antibody directed against ICOS deposited to CNCM on Jul. 2, 2009 under the accession number CNCM I-4180. The inventors have shown that use of said antibody blocks the secretion of IL-10 by Tconv. Said antibody is an antagonist of ICOS and is highly adapted for preventing dendritic cells mediated regulatory T cells expansion and suppressive function in cancer such as breast cancer. The expression "a derivative of 314.8 mAb" refers to an anti-ICOS antibody which comprises the 6 CDRs of 314.8 mAb.

The 6 CDRs of 314.8 mAb are as in Table 2 below:

TABLE 2

| | DNA sequence | Aminoacid sequence |
|---|---|---|
| H-CDR1 | GGCTACACCTTCACCACCTACTG GATGCAC (SEQ ID NO: 1) | GYTFTTYWMH (SEQ ID NO: 7) |

TABLE 2-continued

| | DNA sequence | Aminoacid sequence |
|---|---|---|
| H-CDR2 | GAGATTGATCCTTCTGATAGTTA TGTTAACTACAATCAAAACTTTA AGGGC (SEQ ID NO: 2) | EIDPSDSYVNYNQNFKG TGTTAACTACAATCAAAACTTTA (SEQ ID NO: 8) |
| H-CDR3 | TTTGATTAC (SEQ ID NO: 3) | FDY (SEQ ID NO: 9) |
| L-CDR1 | AGGTCTAGTAAGAGTCCCCTGCA TAGTAACGGCAACATTTACTTAT AT (SEQ ID NO: 4) | RSSKSPLHSNGNIYLY (SEQ ID NO: 10) |
| L-CDR2 | CGGATGTCCAACCTTGCCTCA (SEQ ID NO: 5) | RMSNLAS (SEQ ID NO: 11) |
| L-CDR3 | ATGCAACATCTAGAATATCCGTA CACG (SEQ ID NO: 6) | MQHLEYPYT (SEQ ID NO: 12) |

As used herein, the expression "an antibody of the invention" refers to:
- an antibody directed against ICOS able to neutralize ICOS engagement on Treg by inhibiting the fixation between ICOS and ICOS-L and to abrogate proliferation of Treg induced by plasmacytoid dendritic cells, i.e. an antagonist antibody; as well as
- an antibody directed against ICOS able to induce IL-10 and IFNγ production, to induce CD4$^+$ T cells proliferation; to reduce Tconv proliferation, and to increase the immunosuppressive function of Treg, i.e. an agonist antibody.

Said expression also encompasses any derivatives of said antibodies.

Preferably, the antibodies of the invention are chosen from 53.3 mAb, 88.2 mAb, 92.17 mAb, 145.1 mAb, 145.1 mAb and 314.8 mAb and the derivatives thereof.

As used herein, the expression "antagonist antibody directed against ICOS" refers to an antibody which is able to bind to ICOS without triggering a cellular response similar to the response induced by the naturally occurring ICOS. The expression "the antagonist antibodies of the invention" refers to 145.1 mAb, 314.8 mAb and derivatives thereof.

As used herein, the expression "agonist antibody directed against ICOS" refers to an antibody which is able to bind to ICOS and to trigger a cellular response similar to the response induced by the naturally occurring ICOS. Said antibody thus mimics the action of ICOS. The expression "the agonist antibody of the invention" refers to 53.3 mAb, 88.2 mAb, 92.17 mAb and derivatives thereof.

As used herein, the expressions "antigen presenting cell" and "APC" refer to a class of immune cells capable of internalizing and processing an antigen, so that antigenic determinants are presented on the surface of the cell as MHC-associated complexes, in a manner capable of being recognized by the immune system (e.g., MHC class I restricted cytotoxic T lymphocytes and/or MHC class II restricted helper T lymphocytes). The two requisite properties that allow a cell to function as an APC are the ability to process endocytosed antigens and the expression of MHC gene products. Examples of APC include dendritic cells (DC), mononuclear phagocytes (e.g. macrophages), B lymphocytes, Langerhans cells of the skin and, in humans, endothelial cells.

As used herein, the expressions "Treg" and "Regulatory T cells" refer to a specific population of T lymphocytes that have the capacity to dominantly suppress the proliferation of responder T cells in vitro and inhibit autoimmune diseases. Treg have been implicated as major contributors to the ultimate failure of anti-tumor immune responses in humans. For instance, in ovarian cancer, Treg suppress tumor-specific T cells and high numbers of tumor-associated Treg are associated with reduced survival time. The inventors have shown that Treg selectively inhibit the host immune response and thereby contribute to cancer progression, especially in breast cancer. Treg were originally identified as a CD4$^+$CD25$^+$ cell population, but are also characterized by the expression of the forkhead family transcription factor, FoxP3.

The inventors have shown that Treg proliferate in situ within cancer tissue of a patient and express the cell surface markers ICOS and CD39, compared to Treg extracted from blood of the same patient.

By opposition, the term "Tconv" refers to T cells other than Treg. The term "Tconv" thus includes T cells which function to eliminate antigen (e.g. by producing cytokines which modulate the activation of other cells or by cytotoxic activity). This term includes Thelper cells (e.g. Th1 and Th2 cells) and cytotoxic T cells. In this respect, Thelper cells preferably express CD4 and express low or undetectable levels of CD25. CTL cells preferably express CD8 and low or undetectable levels of CD4. Preferably, a non-Treg cell does not express both CD4 and CD25. Preferably, a non-Treg cell does not express FoxP3.

As used herein, the expressions "tumor associated regulatory T cells" and "Ta-Treg" refer to Regulatory T cells associated with tumors, for example with breast tumors. The inventors have indeed shown that Ta-Treg are present in the lymphoid infiltrates of mammary tumoral tissue and present a negative impact in the survival of the patient suffering from breast cancer.

As used herein, the expressions "plasmacytoid dendritic cells" and "pDC" refer to innate immune cells that circulate in the blood and are found in peripheral lymphoid organs. They constitute a group of cells belonging to the peripheral blood mononuclear cells (PBMC) group.

As used herein, the expressions "Tumor associated plasmacytoid dendritic cells" and "Ta-pDC" refer to plasmacytoid dendridic cells associated with tumors, for example mammary tumors. The inventors have shown that Ta-pDC are able to induce the proliferation of Ta-Treg under the dependence of the ICOS/ICOSL co-stimulation.

As used herein, the terms "IL-10" and "interleukin-10" refer to a human cytokine synthesis inhibitory factor (CSIF), which is an anti-inflammatory cytokine. This cytokine is primarily produced by monocytes and to a lesser extent by lymphocytes. This cytokine has pleiotropic effects in immunoregulation and inflammation. It downregulates the expression of Th1 cytokines, MHC class II antigens. It also enhances B cell survival, proliferation, and antibody production. This cytokine can block NF-κB activity, and is involved in the regulation of the JAK-STAT signaling pathway.

As used herein, the terms "IFNγ" and "interferon-gamma" refer to a dimeric protein with subunits of 146 amino acids. The importance of IFN-γ in the immune system stems in part from its ability to inhibit viral replication directly, and most importantly from its immunostimulatory and immunomodulatory effects. IFNγ is produced predominantly by natural killer (NK) and natural killer T (NKT) cells as part of the innate immune response, and by CD4 and CD8 cytotoxic T lymphocyte (CTL) effector T cells once antigen-specific immunity develops.

As used herein, the terms "treating" or "treatment" means reversing, alleviating, inhibiting the progress of, or preventing the disorder or condition to which such term applies, or one or more symptoms of such disorder or condition.

A "therapeutically effective amount" is intended for a minimal amount of active agent which is necessary to impart therapeutic benefit to a subject. For example, a "therapeutically effective amount" is an amount which induces, ameliorates or otherwise causes an improvement in the pathological symptoms, disease progression or physiological conditions associated with a disease or which improves resistance to a disorder.

As used herein, the term "prevention" refers to alleviating the disease or condition from occurring in a subject which has not yet been diagnosed as having it. As used herein, the term "subject" denotes a mammal, such as a rodent, a feline, a canine, and a primate. Preferably a subject according to the invention is a human.

The term "cancer" includes malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "Treg associated disease" shall be taken to encompass any disease or disorder or state in which modulation of Treg numbers and/or activity may provide a beneficial effect. This term encompasses:
 diseases and conditions associated with Treg mediated suppression of a subject's immune response,
 diseases and conditions associated with or caused by an excessive immune response.

As used herein, the expression "diseases and conditions associated with Treg mediated suppression of immune response" are diseases and conditions caused by the Treg suppression of the proliferation of immunomodulating cells such as tumor-specific T cell. As previously mentioned, the inventors have shown that Treg are associated with a poor diagnostic and survival rate in a patient suffering from cancer.

Non limiting examples of diseases and conditions associated with Treg mediated suppression of a subject's immune system are cancer and chronic infections.

As used herein, "diseases and conditions associated with or caused by an excessive immune response" are for example autoimmune diseases, transplantation rejection or a graft versus host disease.

This expression further encompasses inflammatory conditions, such as inflammatory disorder of the nervous system (e.g. multiple sclerosis), mucosal inflammatory disease (e.g. inflammatory bowel disease, asthma or tonsillitis), inflammatory skin disease (e.g. dermatitis, psoriasis or contact hypersensitivity), autoimmune arthritis (e.g. rheumatoid arthritis).

As used herein, the term "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the body of a subject of cancerous cells, metastatic tumor cells, malignant melanoma, invading pathogens, cells or tissues infected with pathogens, or, in cases of autoimmunity or pathological inflammation, normal cells or tissues of a subject.

As used herein, an "autoimmune disease" is a disease or a disorder arising from and directed against an individual's own tissues.

Antagonist Antibodies of the Invention

It has been shown that ICOS-L, which is a specific ligand of ICOS, is expressed on plasmacytoid dendritic cells. The inventors have shown that Tumor associated Treg were in close contact with Tumor-associated plasmacytoid dendritic cells, indicating that such an interaction allows the engagement of ICOS with ICOS-L in tumors.

They further showed that in situ ICOS/ICOS-L interaction leads to ICOS-L downregulation on the Ta-pDC membrane. The inventors have developed an antagonist antibody directed against ICOS and showed that the addition of said antibody abrogates totally the ICOS-L downregulation on pDC, which is responsible for Ta-Treg activation and proliferation.

The inventors have shown that the antagonist antibody according to the invention neutralizes ICOS engagement on Treg and abrogates their expansion induced by pDC. More precisely, said antibody abrogates Treg proliferation and IL-10 secretion induced by ICOS/ICOSL interaction.

The antagonist antibodies of the invention are thus highly appropriate for abrogating the immunosuppressive response involved in pathological mechanism. They are thus useful for treating diseases and conditions associated with Treg mediated suppression of immune response.

The invention is thus drawn to an antibody directed against ICOS and derivatives thereof which:
 neutralizes ICOS engagement on Treg by inhibiting the fixation between ICOS and ICOS-L; and
 abrogates proliferation of Treg induced by plasmacytoid dendritic cell.

In an embodiment, said antibody is a monoclonal antibody.
In an embodiment, said antibody is a chimeric antibody.
In an embodiment, said antibody is a humanized antibody.

By "neutralizing ICOS engagement on Treg", it is meant that the antibody interferes with the cooperation between ICOS and its ligand ICOS-L.

By "abrogating proliferation of Treg", it is meant that a significant decrease, preferably a total stop, of the proliferation of Treg is observed in a target tissue, preferably a tumor tissue, as compared to a control tissue, preferably a non-tumor tissue, more preferably blood.

The invention further relates to an antibody directed against ICOS, wherein said antibody is selected from the group consisting of Icos 145-1 and Icos 314-8, respectively obtainable from the hybridoma deposited at the CNCM on Jul. 2, 2009 under the accession numbers CNCM I-4179 and CNCM I-4180 and derivatives thereof.

The invention also relates to an antibody which comprises the 6 CDRs of an antibody selected from the group consisting of Icos 145-1 and Icos 314-8, respectively obtainable from the hybridoma deposited at the CNCM on Jul. 2, 2009 under the accession numbers CNCM I-4179 and CNCM I-4180 and derivatives thereof.

The invention also relates to an antibody which comprises the 6 CDRs of Table 2 above.

In another embodiment, the invention relates to a derivative antibody of one of the antibodies selected from the group consisting of Icos 145-1 and Icos 314-8, respectively obtainable from the hybridoma deposited at the CNCM on Jul. 2, 2009 under the accession numbers CNCM I-4179 and CNCM I-4180.

Therapeutic Use of Antagonist Antibodies of the Invention

By neutralizing ICOS engagement on Treg and abrogating proliferation of Treg, the antagonist antibodies of the invention are highly appropriate for use for treating diseases and conditions associated with Treg mediated suppression of immune response, for example cancers and chronic infections. Said antibodies may thus be used for restoring an anti-tumor immunity.

The invention therefore relates to the antagonist antibody directed against ICOS according to the invention or a derivative thereof for use as a medicament.

The invention further relates to the antagonist antibody directed against ICOS according to the invention or a derivative thereof for use for treating disease or a condition associated with Treg mediated suppression of immune response.

In a preferred embodiment, said disease or a condition associated with Treg mediated suppression of immune response is a disease selected in the group consisting of cancers and chronic infections.

Indeed, the inventors have shown that the antagonist antibodies of the invention are adapted for modulating Treg numbers and/or activity so that to abrogate the immunosuppressive effect related to those Treg. Therefore, said antagonist antibodies represent a highly promising strategy for treating diseases associated with a suppression of immune system such as cancer and chronic infections.

Examples of cancers include, but are not limited to human malignant lymphoma, breast cancer, ovarian cancer, colon cancer lung cancer, brain cancer, prostate cancer, head and neck cancer, pancreatic cancer, bladder cancer, colorectal cancer, bone cancer, cervical cancer, liver cancer, oral cancer, esophageal cancer, thyroid cancer, kidney cancer, stomach cancer, testicular cancer and skin cancer.

Examples of chronic infections include, but are not limited to, viral, bacterial, parasitic or fungal infections such as chronic hepatitis, lung infections, lower respiratory tract infections, bronchitis, influenza, pneumoniae and sexually transmitted diseases.

Examples of viral infections include, but are not limited to, hepatitis (HAV, HBV, HCV), herpes simplex (HSV), herpes zoster, HPV, influenza (Flu), AIDS and AIDS related complex, chickenpox (varicella), common cold, cytomegalovirus (CMV) infection, smallpox (variola), Colorado tick fever, dengue fever, ebola hemorrhagic fever, foot and mouth disease, lassa fever, measles, marburg hemorrhagic fever, infectious mononucleosis, mumps, norovirus, poliomyelitis, progressive multifocal leukencephalopathy (PML), rabies, rubella, SARS, viral encephalitis, viral gastroenteritis, viral meningitis, viral pneumonia, West Nile disease and yellow fever.

Examples of bacterial infections include, but are not limited to, pneumonia, bacterial meningitis, cholera, diphtheria, tuberculosis, anthrax, botulism, brucellosis, campylobacteriosis, typhus, gonorrhea, listeriosis, lyme disease, rheumatic fever, pertussis (Whooping Cough), plague, salmonellosis, scarlet fever, shigellosis, syphilis, tetanus, trachoma, tularemia, typhoid fever, and urinary tract infections.

Examples of parasitic infections include, but are not limited to, malaria, leishmaniasis, trypanosomiasis, chagas disease, cryptosporidiosis, fascioliasis, filariasis, amebic infections, giardiasis, pinworm infection, schistosomiasis, taeniasis, toxoplasmosis, trichinellosis, and trypanosomiasis. Examples of fungal infections include, but are not limited to, candidiasis, aspergillosis, coccidioidomycosis, cryptococcosis, histoplasmosis and tinea pedis.

In a preferred embodiment of the invention, the invention relates to the antagonist antibodies directed against ICOS according to the invention or a derivative thereof for use for treating cancer. Preferably, said cancer is selected from human malignant lymphoma, ovarian cancer, cervical cancer and breast cancer. Most preferably, said cancer is breast cancer.

The invention also relates to a method for treating disease or a condition associated with Treg mediated suppression of immune response is a disease selected in the group consisting of cancers and chronic infections, preferably cancers and chronic infections, preferably cancers, wherein said method comprises the step of administering to a subject in need thereof a therapeutically effective amount of an antagonist antibody directed against ICOS according to the invention or a derivative thereof.

Agonist Antibodies Directed Against ICOS

ICOS engagement has been found to be associated with an immunosuppressive T cell response. Indeed, said engagement has been described to reduce IL-10 and IFNγ production and to reduce $CD4^+$ T cell proliferation.

Therefore, as evidenced by the inventors, an agonist antibody of ICOS provides the opposite effect and is beneficial for treating diseases associated with or caused by an excessive immune response. The invention thus relates to an antibody directed against ICOS or a derivative thereof which:

induces IL-10 and IFNγ production;
induces CD4+ T cell proliferation;
reduces Tconv proliferation, and
increases the immunosuppressive function of Treg.

By "inducing IL-10 and IFNγ production", it is meant that a significant increase of the production of IL-10 and IFNγ is observed.

By "inducing CD4+ T cell proliferation", it is meant that a significant increase of the proliferation of CD4+ T cells is observed in a target tissue, preferably a tumor tissue, as compared to a control tissue, preferably a non-tumor tissue, more preferably blood.

By "reducing Tconv proliferation", it is meant that a significant decrease of the proliferation of Tconv is observed in a target tissue, preferably a tumor tissue, as compared to a control tissue, preferably a non-tumor tissue, more preferably blood.

By "increasing the immunosuppressive function of Treg", it is meant that a significant increase of the Treg suppressive activity is observed.

In an embodiment, said antibody is a monoclonal antibody.
In an embodiment, said antibody is a chimeric antibody.
In an embodiment, said antibody is a humanized antibody.

The invention further relates to an antibody directed against ICOS, wherein said antibody is selected from the group consisting of Icos 53-3, Icos 88-2 and Icos 92-17, respectively obtainable from the hybridoma deposited at the CNCM on Jul. 2, 2009 under the accession numbers CNCM I-4176, CNCM I-4177, CNCM I-4178 and derivatives thereof.

The invention also relates to an antibody which comprises the 6 CDRs of an antibody selected from the group consisting of Icos 53-3, Icos 88-2 and Icos 92-17 respectively obtainable from the hybridoma deposited at the CNCM on Jul. 2, 2009 under the accession numbers CNCM I-4176, CNCM I-4177, CNCM I-4178.

The invention also relates to an antibody which comprises the 6 CDRs of Table 1 above.

In another embodiment, the invention relates to a derivative antibody of one of the antibodies selected from the group consisting of Icos 53-3, Icos 88-2 and Icos 92-17, respectively obtainable from the hybridoma deposited at the CNCM on Jul. 2, 2009 under the accession numbers CNCM I-4176, CNCM I-4177, CNCM I-4178.

Therapeutic Use of Agonist Antibodies of the Invention

The invention also relates to the agonist antibody directed against ICOS according to the invention or a derivative thereof for use as a medicament.

The invention is also drawn to the agonist antibody directed against ICOS according to the invention or a derivative thereof for use for treating a disease or a condition associated with or caused by an excessive immune response.

The invention is also drawn to the agonist antibody directed against ICOS according to the invention or a derivative thereof for use for treating an autoimmune disease, transplantation rejection or a graft versus host disease.

In one particular embodiment, said autoimmune disease is selected from the group consisting of rheumatoid arthritis (RA), insulin dependent diabetes mellitus (Type 1 diabetes), multiple sclerosis (MS), Crohn's disease, systemic lupus erythematosus (SLE), scleroderma, Sjogren's syndrome, pemphigus vulgaris, pemphigoid, addison's disease, ankylosing spondylitis, aplastic anemia, autoimmune hemolytic anemia, autoimmune hepatitis, coeliac disease, dermatomyositis, Goodpasture's syndrome, Graves' disease, Guillain-Barre syndrome, Hashimoto's disease, idiopathic leucopenia, idiopathic thrombocytopenic purpura, male infertility, mixed connective tissue disease, myasthenia gravis, pernicious anemia, phacogenic uveitis, primary biliary cirrhosis, primary myxoedema, Reiter's syndrome, stiff man syndrome, thyrotoxicosis, ulceritive colitis, and Wegener's granulomatosis.

In another embodiment, the invention is also drawn to the agonist antibody directed against ICOS according to the invention or a derivative thereof for use for treating an inflammatory disorder selected in the group consisting of inflammatory disorder of the nervous system such as multiple sclerosis, mucosal inflammatory disease such as inflammatory bowel disease, asthma or tonsillitis, inflammatory skin disease such as dermatitis, psoriasis or contact hypersensitivity, and autoimmune arthritis such as rheumatoid arthritis.

The invention also relates to a method for treating a disease or a condition associated with or caused by an excessive immune response, preferably an autoimmune disease, a transplantation rejection, a graft versus host disease, or a inflammatory disorder wherein said method comprises the step of administering to a subject in need thereof a therapeutically effective amount of an agonist antibody directed against ICOS according to the invention or a derivative thereof.

Nucleic Acid Sequence Encoding an Antibody of the Invention

A further embodiment of the invention relates to a nucleic acid sequence encoding an antibody one of the antibodies selected from the group consisting of 53.3 mAb, 88.2 mAb, 92.17 mAb, 145.1 mAb, 314.8 mAb and derivatives thereof.

In a particular embodiment, the invention relates to a nucleic acid sequence encoding the VH domain or the VL domain of one of the antibodies selected from the group consisting of 53.3 mAb, 88.2 mAb, 92.17 mAb, 145.1 mAb, 314.8 mAb and derivatives thereof.

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. So, a further object of the invention relates to a vector comprising a nucleic acid of the invention. Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40, LTR promoter and enhancer of Moloney mouse leukemia virus, promoter and enhancer of immunoglobulin H chain and the like.

Any expression vector for animal cell can be used, so long as a gene encoding the human antibody C region can be inserted and expressed. Examples of suitable vectors include pAGE107, pAGE103, pHSG274, pKCR, pSG1 beta d2-4- and the like. Other examples of plasmids include replicating plasmids comprising an origin of replication, or integrative plasmids, such as for instance pUC, pcDNA, pBR, and the like. Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

A further object of the present invention relates to a cell which has been transfected, infected or transformed by a nucleic acid and/or a vector according to the invention. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed". The nucleic acids of the invention may be used to produce an antibody of the invention in a suitable expression system. The term "expression system" means a host cell and compatible vector under suitable conditions, e.g. for the expression of a protein coded for by foreign DNA carried by the vector and introduced to the host cell.

Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g. Vero cells, CHO cells, 3T3 cells, COS cells, etc.) as well as primary or established mammalian cell cultures (e.g. produced from lymphoblasts, fibroblasts, embryonic cells, epithelial cells, nervous cells, adipocytes, etc.). Examples also include mouse SP2/0-Ag14 cell (ATCC CRL1581), mouse P3×63-Ag8.653 cell (ATCC CRL1580), CHO cell in which a dihydrofolate reductase gene (hereinafter referred to as "DHFR gene") is defective, rat YB2/3HL.P2.G11.16Ag.2O cell (ATCC CRL1662, hereinafter referred to as "YB2/0 cell"), and the like.

The present invention also relates to a method of producing a recombinant host cell expressing an antibody according to the invention, said method comprising the steps of:

(i) introducing in vitro or ex vivo a recombinant nucleic acid or a vector as described above into a competent host cell, (ii) culturing in vitro or ex vivo the recombinant host cell obtained, and (iii) optionally, selecting the cells which express and/or secrete said antibody.

Such recombinant host cells can be used for the production of antibodies of the invention.

Pharmaceutical Composition According to the Invention

The invention also relates to pharmaceutical compositions comprising an antibody of the invention.

Therefore, an antibody of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment. To prepare pharmaceutical compositions, an effective amount of the antibody may be dissolved or dispersed in a pharmaceutically acceptable carrier or aqueous medium. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An antibody of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization.

Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose.

These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibodies of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered. In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 µm) are generally designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 µm. Sonication of MLVs results in the formation of small unilamellar vesicles (SUVs) with diameters in the range of 200 to 500 A, containing an aqueous solution in the core. The physical characteristics of liposomes depend on pH, ionic strength and the presence of divalent cations.

Method for Producing Antibodies of the Invention

Antibodies of the invention may be produced by any technique known in the art, such as, without limitation, any chemical, biological, genetic or enzymatic technique, either alone or in combination.

Knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

In particular, the invention further relates to a method of producing an antibody of the invention, which method comprises the steps consisting of:

(i) culturing a transformed host cell according to the invention under conditions suitable to allow expression of said antibody; and (ii) recovering the expressed antibody.

In another particular embodiment, the method comprises the steps of:

(i) culturing the hybridoma deposited as CNCM I-4176, CNCM I-4177, CNCM I-4178, CNCM I-4179, or CNCM I-4180 under conditions suitable to allow expression of the antibody; and (ii) recovering the expressed antibody.

Antibodies of the invention are suitably separated from the culture medium by conventional immunoglobulin purification procedures such as, for example, protein A-Sepharose, hydroxylapatite chromatography, gel electrophoresis, dialysis, or affinity chromatography.

In a particular embodiment, the human chimeric antibody of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell. As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used. Methods for producing chimeric antibodies involve conventional recombinant DNA and gene transfection techniques are well known in the art (See patent documents U.S. Pat. No. 5,202,238; and U.S. Pat. No. 5,204, 244).

The humanized antibody of the present invention may be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell.

The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into animal cells, and balance between the expression levels of antibody H and L chains in animal cells, humanized antibody expression vector of the tandem type is preferred. Examples of tandem type humanized antibody expression vector include pKANTEX93 (WO 97/10354), pEE18 and the like.

Methods for producing humanized antibodies based on conventional recombinant DNA and gene transfection techniques are well known in the art. Antibodies can be humanized using a variety of techniques known in the art including, for example, CDR-grafting (EP 239,400; PCT publication WO91/09967; U.S. Pat. Nos. 5,225,539; 5,530,101; and 5,585,089), veneering or resurfacing (EP 592,106; EP 519, 596), and chain shuffling (U.S. Pat. No. 5,565,332). The general recombinant DNA technology for preparation of such antibodies is also known (see European Patent Application EP 125023 and International Patent Application WO 96/02576).

The Fab of the present invention can be obtained by treating an antibody which specifically reacts with ICOS with a protease, papaine. Also, the Fab can be produced by inserting DNA encoding Fab of the antibody into a vector for prokaryotic expression system, or for eukaryotic expression system, and introducing the vector into a procaryote or eucaryote (as appropriate) to express the Fab.

The F(ab')2 of the present invention can be obtained treating an antibody which specifically reacts with ICOS with a protease, pepsin.

Also, the F(ab')2 can be produced by binding Fab' described below via a thioether bond or a disulfide bond.

The Fab' of the present invention can be obtained by treating F(ab')2 which specifically reacts with human ICOS with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well known technology called CDR grafting may be used, which involves selecting the complementary determining regions (CDRs) from a donor scFv fragment, and grafting them onto a human scFv fragment framework of known three dimensional structure (see, e.g., WO98/45322; WO 87/02671; U.S. Pat. No. 5,859,205; U.S. Pat. No. 5,585,089; U.S. Pat. No. 4,816,567; EP0173494).

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce of the binding activity.

In order to resolve the problem, in antibodies grafted with human CDR, attempts have to be made to identify, among amino acid sequences of the FR of the VH and VL of human antibodies, an amino acid residue which is directly associated with binding to the antibody, or which interacts with an amino acid residue of CDR, or which maintains the three-dimensional structure of the antibody and which is directly associated with binding to the antigen. The reduced antigen binding activity could be increased by replacing the identified amino acids with amino acid residues of the original antibody derived from a non-human animal.

Modifications and changes may be made in the structure of the antibodies of the present invention, and in the DNA sequences encoding them, and still obtain a functional molecule that encodes an antibody with desirable characteristics. In making the changes in the amino sequences, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

A further embodiment of the present invention also encompasses function-conservative variants of the antibodies of the present invention.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like).

Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm.

A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared. Two amino acid sequences are "substantially homologous" or "substantially similar" when greater than 80%, preferably greater than 85%, preferably greater than 90% of the amino acids are identical, or greater than about 90%, preferably grater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said antibodies, without appreciable loss of their biological activity.

It is known in the art that certain amino acids may be substituted by other amino acids having a similar hydropathic index or score and still result in a protein with similar biological activity, i.e. still obtain a biological functionally equivalent protein. As outlined above, amino acid substitutions are generally therefore based on the relative similarity of the amino acid side-chain substituents, for example, their hydrophobicity, hydrophilicity, charge, size, and the like.

Exemplary substitutions which take various of the foregoing characteristics into consideration are well known to those of skill in the art and include: arginine and lysine; glutamate and aspartate; serine and threonine; glutamine and asparagine; and valine, leucine and isoleucine. Another type of amino acid modification of the antibody of the invention may be useful for altering the original glycosylation pattern of the antibody.

By "altering" is meant deleting one or more carbohydrate moieties found in the antibody, and/or adding one or more glycosylation sites that are not present in the antibody.

Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites). Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. For example, such methods are described in WO87/05330.

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact.

Enzymatic cleavage of carbohydrate moieties on antibodies can be achieved by the use of a variety of endo- and exo-glycosidases.

Another type of covalent modification of the antibody comprises linking the antibody to one of a variety of non proteinaceous polymers, eg., polyethylene glycol, polypropylene glycol, or polyoxyalkylenes, in the manner set forth in U.S. Pat. No. 4,640,835; 4,496, 689; 4,301, 144; 4,670, 417; 4,791, 192 or 4,179,337. It may be also desirable to modify the antibody of the invention with respect to effector function, e.g. so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing inter-chain disulfide bond formation in this region. The homodimeric antibody thus generated may have improved internalization capability and/or increased complement-mediated cell killing and/or antibody-dependent cellular cytotoxicity (ADCC) (Caron P C. et al. J Exp Med. 1992 Oct. 1; 176(4):1191-5 and Shopes B. J Immunol. 1992 May 1; 148 (9):2918-22).

Diagnostic Method

The present invention also relates to a diagnostic method of an increased risk of relapse or early death in a breast cancer patient. Indeed, as shown in Example 3, the presence of high $ICOS^+$ Treg cells number is associated to lower Progression Free Survival or Overall Survival for breast cancer patients.

Thus, the invention relates to a method for diagnosing an increased risk of relapse or early death in a breast cancer patient, comprising the step of quantifying ICOS positive ($ICOS^+$) Treg cells in a sample of said patient. If said number is high, for example greater than 1.7 $ICOS^+$ cells/spot when using the method of example 3 and FIG. 9, then there is an increased risk of relapse or early death in said breast cancer patient.

The invention also relates to a method for selecting patients susceptible of being treated by anti-ICOS immunotherapy, comprising the step of quantifying ICOS positive Treg cells in a sample of said patient. Said immunotherapy may be anti-ICOS antibodies of the invention.

Said sample may come from a biopsy. Said quantification of $ICOS^+$ Treg cells may be performed thanks to anti ICOS antibodies, especially thanks to any one of the antibodies described above.

Treatment in Pre-Clinical Mammary Tumor Model

As shown in Example 6, treatment of an established murine model of mammary tumor with a surrogate neutralizing rat anti murine ICOS antibody (17G9, IgG2b), reduces tumor progression, reenforcing the potential of treatment with anti-ICOS neutralizing antibodies of the invention to favor of tumor regression in the subpopulation of patients with high $ICOS^+$ Treg detection in their primary breast tumor.

The invention will further be illustrated in view of the following figures and example.

FIGURE LEGEND

FIG. 1: Ta-Treg strongly express ICOS, co-localized with Ta-pDC and proliferate in situ but do not proliferate in vitro.

A—Tumor frozen sections were stained with anti ICOS Ab (green) and Ki67 Ab (brown) and secondary anti murine Ab conjugated to HRP and revealed respectively with histogreen and DAB (magnification 10× and 40× for the insert box)).

B—Ki67 expression) was analyzed by multi color flow cytometry on Treg ($CD4^+CD127^-CD25^{high}$) and Tconv ($CD4^+CD127^+CD25^{low/-}$) within primary tumor (Ta-Treg, Ta-Tconv) or paired blood (Treg, Tconv).

C—Purified Treg and Tconv from either primary tumor or healthy blood were cultured in a 96 well U-bottomed-plate in presence of 500 UI/ml of IL-2. Cell number was quantified every 4 days by enumeration.

D-F Tumor frozen sections were stained with anti CD3 Ab (brown) and counterstained with hematoxylin (blue) (10× and 40× in the insert box) (D); CD3 Ab (green) and BDCA2 (brown) (20× and 40× in the insert box) (E); FoxP3 Ab (brown) and BDCA2 (green) (20× and 40×n the insert box) (F).

Figure 2:
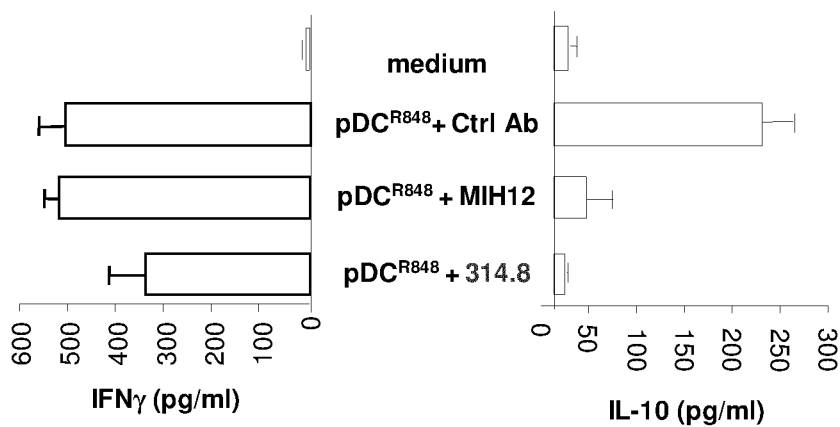
Figure 2:
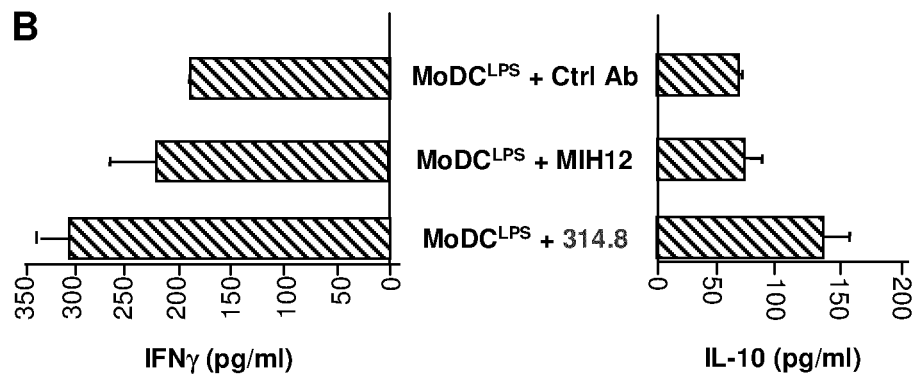

FIG. 2: ICOS and ICOS-L blockade abrogates IL-10 secretion during pDC mediated T cell activation without interfering strongly on MoDC/T co-culture. Purified and R848-activated pDC or MoDC were co-cultured for 5 days with allogeneic memory $CD4^+$ T cells in presence of Ctrl Ab, anti ICOS (314.8) or anti ICOS-L (MIH12). At day 5, IL-10 and IFNγ were quantified by ELISA in supernatants from pDC/T co-culture (A) and MoDC/T co-culture (B).

Figure 3:
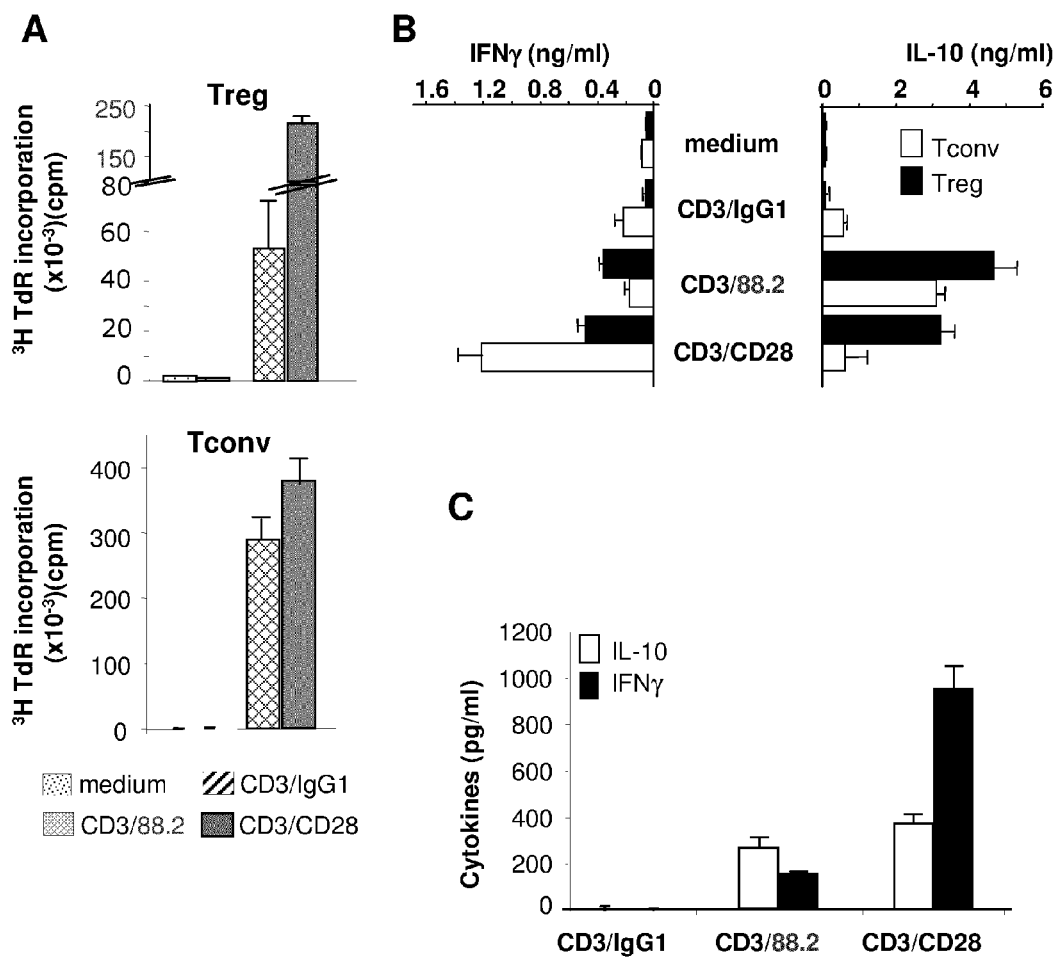

FIG. 3: ICOS and CD3 co-stimulation favor Treg and Tconv proliferation as well as IL-10 but not IFNγ secretion in the presence of exogenous IL-2.

A/B—FACS-sorted Treg or Tconv issued from tonsil were cultured for 5 days alone or with beads coated with CD3/IgG, CD3/88.2, CD3/CD28 agonist mAb in the presence of IL-2 (n=3). The proliferation was assessed by [$^3$H]-Thymidine incorporation (A). IL-10 and IFNγ levels were measured by ELISA in the culture supernatant (B).

C—$CD4^+$ TaT cells sorted from tumor were cultured for 5 days with beads coated with antiCD3/IgG; antiCD3/88.2 or antiCD3/antiCD28 in the presence of exogenous IL-2 (100 UI/ml). The concentrations of IL-10 and IFNγ in the supernatant were quantified by ELISA.

Figure 4:
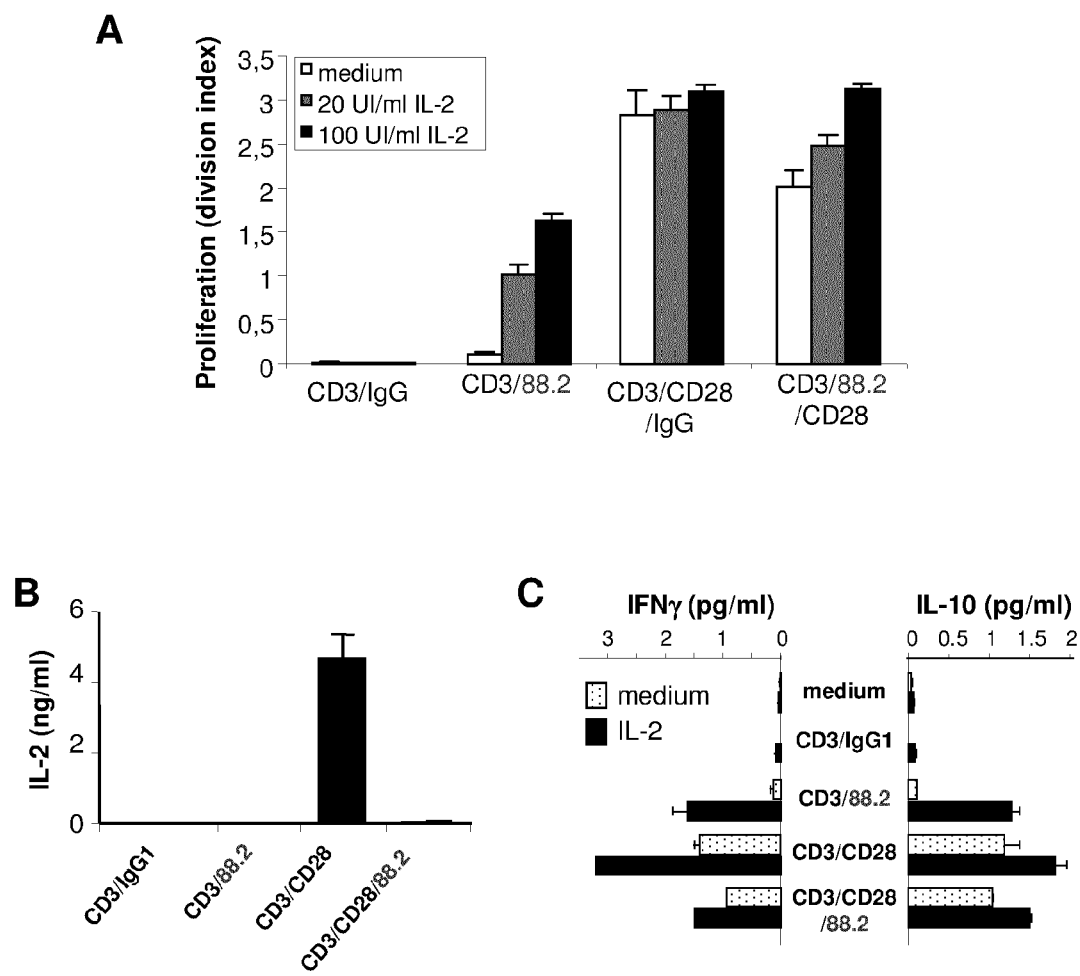

FIG. 4: ICOS engagement blocks CD28-induced IL-2 and consequently reduces proliferation and IFNγ secretion A—CFSE labeled $CD4^+$ memory T cells were cultured for 5 days with the different beads alone or in presence of graded concentration of exogenous rhIL-2 (20 UI/ml and 100 UI/ml) and proliferation was assessed by CFSE dilution by flow cytometry.

B—IL-2 detected by ELISA after 5 days culture with the different beads without exogenous IL-2.

C— Blood $CD4^+$ memory T lymphocytes from healthy donors were cultured for 5 days with the different beads alone or in presence of exogenous IL-2 (100 UI/ml). The IL-10 and IFNγ secretions were quantified by ELISA.

Figure 5:
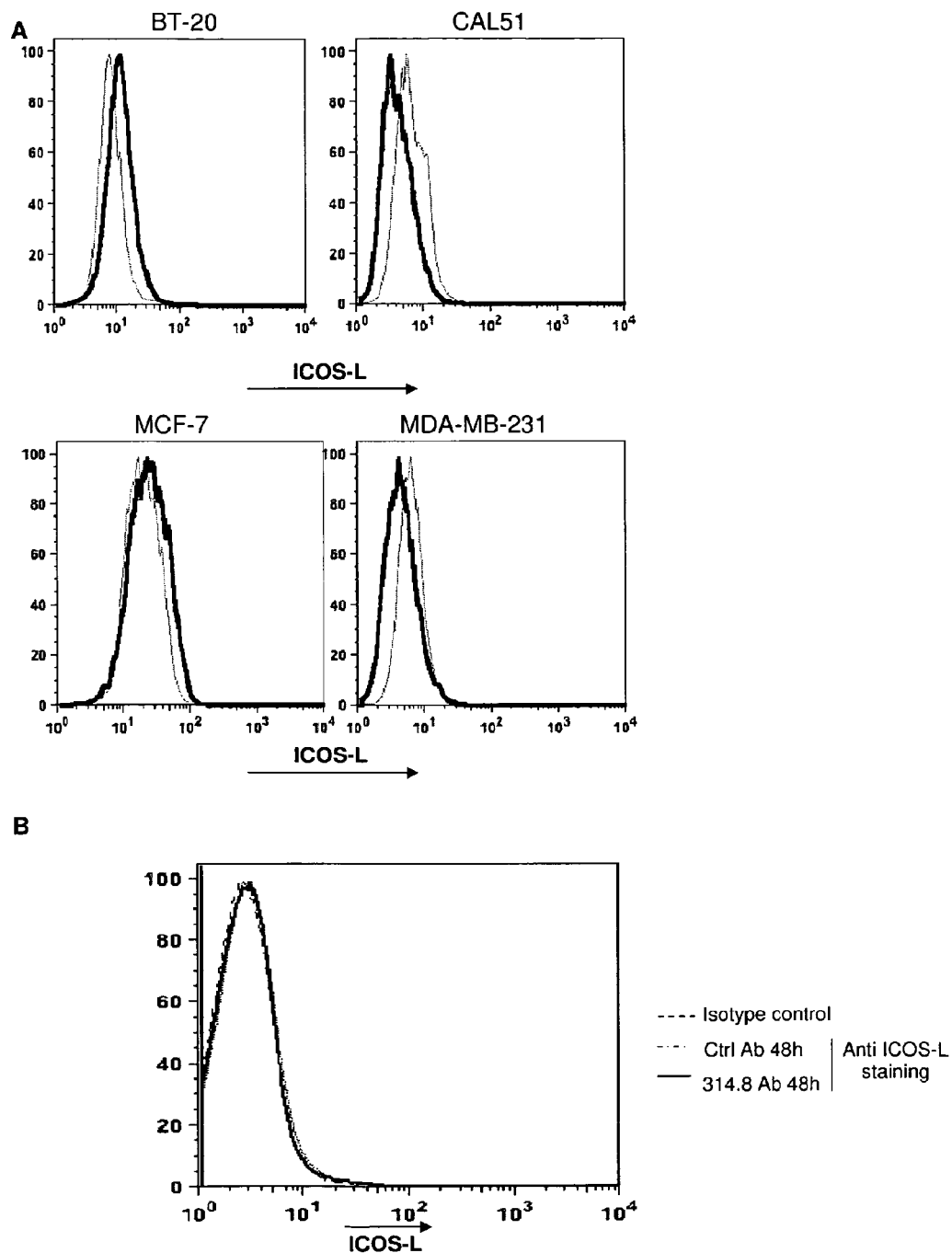

FIG. 5: Absence of expression of ICOS-L on breast tumor cell lines and primary breast tumor dilacerations A—ICOS-L expression was assessed by flow cytometry on breast tumor epithelial cell lines suspensions harvested in PBS-EDTA in absence of trypsin to avoid Ag deterioration.

B—ICOS-L expression was assessed on tumor cells (CD45− cells) after 48 h culture in presence of control Ab (dashed line) or anti ICOS Ab (314.8) (continuous line).

Figure 6:
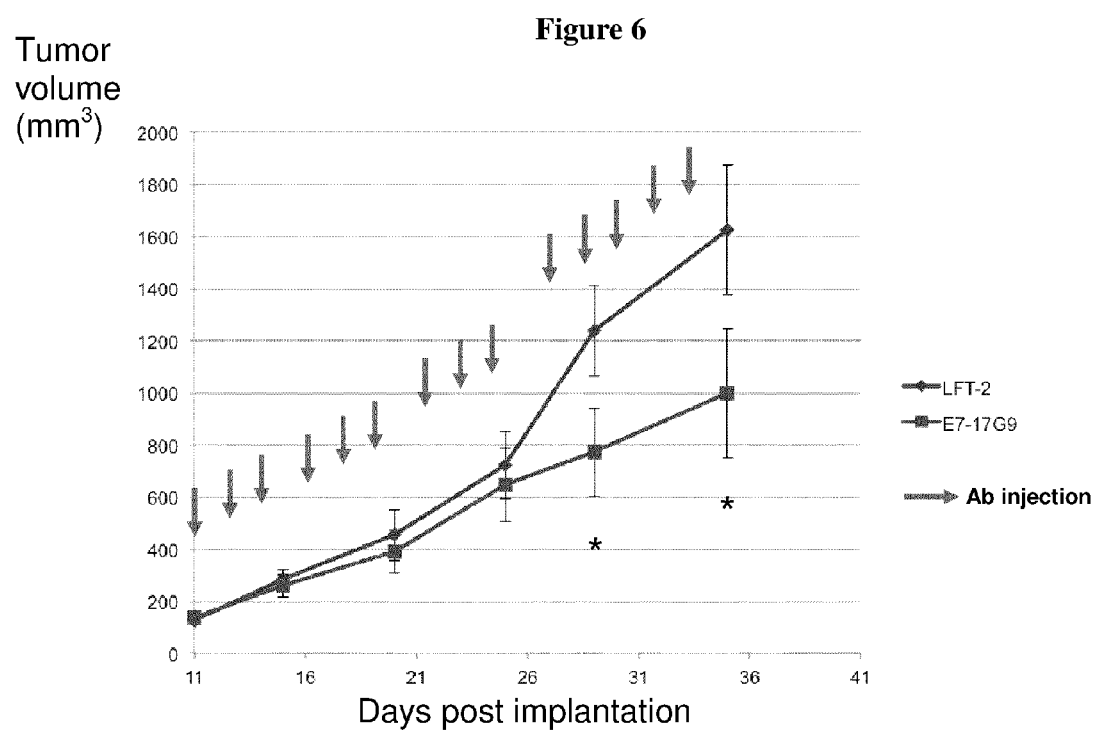

FIG. 6: Treatment of primary Neu15 mammary tumors with a surrogate rat anti-mouse anti ICOS Ab (17G9, IgG2b) slow down the tumor growth.

FIG. 7:

A: Treg cells numbers are increased within primary cervix cancer.

B: Treg cells ICOS+ are increased within primary cervix cancer.

Figure 8:
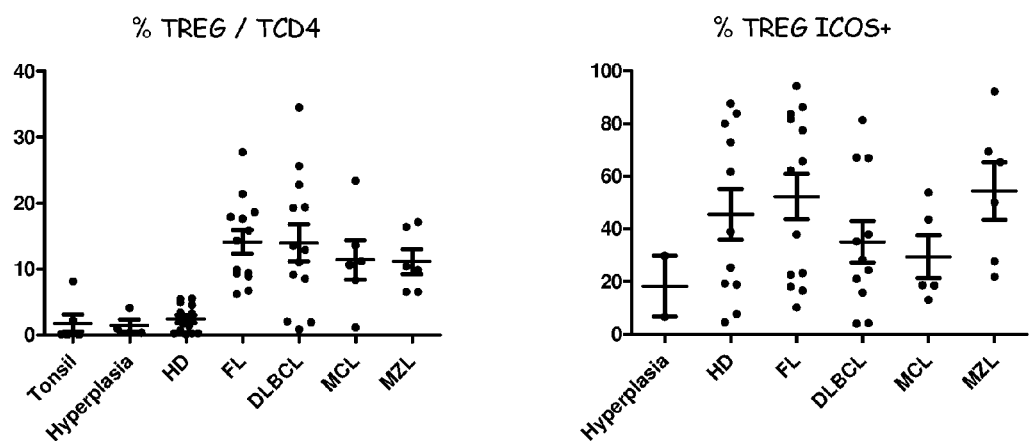

FIG. 8: Increase of ICOS expressing Treg in non Hodgkin lymphoma (NHL)

Figure 9:
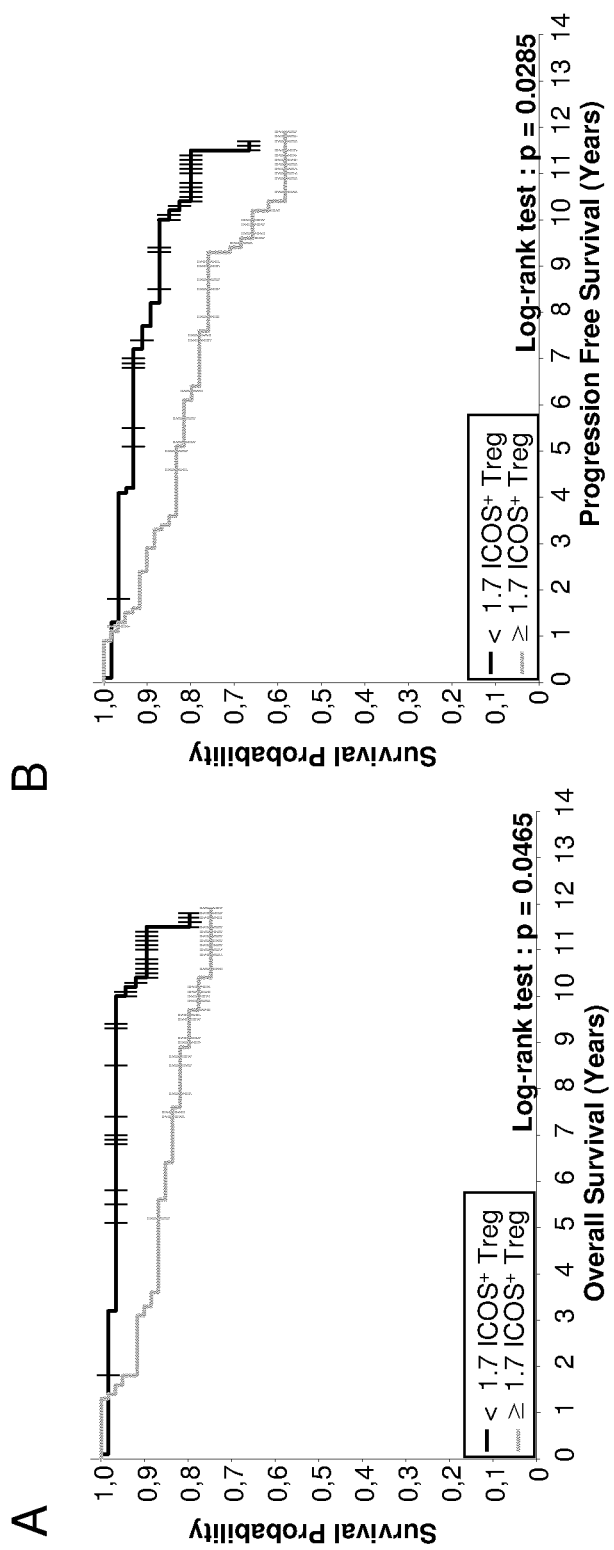

HD Hodgkin Disease
FL Follicular Lymphoma
DLBCL Diffuse Large B Cell Lymphoma
MCL Mantle Cell Lymphoma
MZL Marginal Zone Lymphoma FIG. 9: Presence of ICOS+ Treg cells within primary breast tumors has a negative impact on survival 120 paraffin embedded primary tumor samples with 10 years clinical follow up were tested for their expression of ICOS using a commercial anti ICOS rabbit polyclonal Ab. Mean of ICOS+ cells were assessed on six different spots. To perform the statistical analysis the median was used as cut-off to have equilibrated groups.

Impact of ICOS expression according to the presence of ICOS in the primary tumor on Overall Survival (A) or Progression Free Survival (B) is shown.

EXAMPLE

Example 1

Characterisation of the Antibodies According to the Invention

Material and Methods

I. Cellular Biology

1—Selection/Cell Purification

Isolation of Peripheral Blood Mononuclear Cells

PBMCs (Peripheral Blood Mononuclear Cells) were isolated from peripheral stem cells transplantation of healthy volunteers (Etablissement Francais du sang, Marseille, France) by Lymphoprep gradient (Abcys). In tubes: ⅔ of blood are deposited dropwise over ⅓ of Lymphoprep and centrifuged for 20 minutes at 2000 rpm at 20° C. with no acceleration so as not to disturb the gradient. After centrifugation, the mononuclear cells are recovered and washed twice in PBS 1% FCS (Fetal Calf Serum)+heparin for 20 min at 1000 rpm at 20° C.

The cells were then used immediately or frozen at −80° C. to $50 \cdot 10^6$ cells/ml in RPMI 1640 50% FCS 10% DMSO (Dimethyl Sulfoxide). After 24 h, the cells are transferred to the nitrogen for preservation Negative Selection of CD4

CD4+ T lymphocytes were purified from PBMCs. After thawing, the cells were washed and diluted in 40 µL of sorting buffer (PBS 0.5% BSA 2 mM EDTA) for $10 \cdot 10^6$ cells. The kit MACS human CD4+ T Cell Isolation Kit II were used (Miltenyi Biotec): 10 µL of a solution of monoclonal antibodies conjugated to biotin (primary labeling) are added and the mixture was incubated for 10 min at 4° C. with stirring.

The cells are then put in contact with 20 µL of magnetic beads coupled with anti-biotin (secondary labeling) for 15 min at 4° C. with stirring. After washing with buffer sorting, cells were sorted to Automacs (Miltenyi). The negative fraction depleted in CD4+ T labeled cells is then isolated. This gives a population of CD4+ pure of about 95%.

2—Activation and Cell Culture

Pre-Activation with Beads CD3/CD28 and then Stimulation with mAbs

The CD4+ T cells are put to the concentration of $10^6$ cells/mL RPMI 10% FCS in the presence of beads CD3/CD28 (Dynabeads, Invitrogen) (1 cell/1 bead) and incubated for 48 h at 37° C. The cells are then separated from the beads with a magnet and Dynal Biotech rest overnight in RPMI 10% FCS at a concentration of $10^6$ cells/ml.

On the other hand, mAbs anti-CD3 (OKT3), anti-ICOS (ICOS 88-2), and control IgG1 mAb (Sigma) were coated on a 96 flat well overnight at 4° C. The wells are coated with 50 ng/ml anti-CD3 supplemented with 20 µg/ml in other mAbs PBS 1×100 µL/wells. The next day, the plate is washed with PBS, saturated two hours with PBS 5% FCS (200 µl per well). The CD4+ T cells with the previously incorporated CFSE (see below) are distributed on the coated plate at a rate of 2 105 cells/200 µL, of medium/well and incubated for 72 h at 37° C. At 48 h, supernatants were collected and at 72 h, cells were collected to analyze proliferation by flow cytometry (FIG. 4).

Activation by Artificial APC

Magnetic beads (Dynabeads M-450 Epoxy, Invitrogen) were washed in sodium phosphate buffer 0.1M and then incubated with mAbs anti-CD3 (OKT3) at a concentration suboptimal of $1 \text{ mg}/1 \cdot 10^7$ beads representing 5% of the mAbs coupled with the beads, with the mAb anti-CD28 or ICOS (ICOS 88-2 or CD28.2), ($2 \text{ µg}/1 \cdot 10^7$ beads, 10%). These artificial APC were incubated with mAbs in slow rotation overnight at 4° C. The next day, two washes are performed in PBS 0.1% BSA. Artificial APC are distributed on a one bead for a cell in a 96 round plate wells on which $2 \cdot 10^5$ lymphocytes T CD4+/200 µl per well were deposited and then incubated for 72 h at 37° C. The CD4+ T cells have previously incorporated the CFSE. At 48 h, supernatants were collected and 72 h, cells were collected to analyze proliferation by flow cytometry.

3—Cell Proliferation

The proliferation of lymphocytes is followed by the CFSE (carboxyfluorescein diacetate succinimidyl ester) (Molecular Probes, Invitrogen). The CFSE is cell permeable and nonfluorescent. When entering the cell, esterases cleave the acetate groups which become fluorescent whereas the cell become impermeable.

The characteristic of CFSE is to be shared equitably in each newly formed cell at each division. It emit in the green radiation allows the simultaneously analyze of the number, the position and the stage of differentiation of the cells, the fluorescence intensity per cell being proportional to the concentration of CFSE. To label the cells with CFSE, the cell suspension is diluted in cold 1×PBS. Adding the CFSE: 5 µM to $10 \cdot 10^6$ cells. The cells are then placed in a water-bath at 37° C.

After 8 to 10 minutes stirring, the cells were quickly placed on ice to stop the reaction. The cells are then centrifuged twice with 2 ml of PBS 1×. Finally they are collected in the desired volume of RPMI 10% FCS for culture. The proliferation is determined thanks to flow cytometry.

II—Flow Cytometry

CD4+ cells are diluted with 30% BSA PBS (50 µL/well) in a 96-well plate for 10 minutes at 4° C. to saturate nonspecific sites. They are then incubated for 30 minutes at 4° C. in the dark, with the desired antibodies coupled to a fluorochrome.

After two washes in PBS 1×1% BSA 0.02% azide (centrifugation 2100 rpm, 3 min at 4° C.), cells were fixed in 200 µL of PBS 2% formaldehyde and placed in a flow cytometer (FACS Canto, BD Biosciences). The results are analyzed thanks to the FlowJo software.

III—ELISA (Enzyme Linked Immunosorbent Assay)

Culture supernatants of CD4+ T cells are collected at 48 h and stored at −20° C. for an assay on IL-10, IFNγ and TNFα.

Results

1—Characterization of Anti-ICOS mAbs

The inventors developed 5 anti-ICOS Abs. Their isotype was assayed by ELISA. For obtaining an indirect analysis of their affinity for their receptor, mAbs were tested using stable transfectants expressing ICOS. JICOS.1 cells were in the presence of an increasing range of anti-ICOS mAbs labeled with a probe coupled to a fluorochrome (PE-GAM: Goat anti mouse-PE) and the analysis was made thanks to cytometry flow.

It was thus possible to determine the ED 50, i.e. the concentration of mAbs which 50% of sites are saturated. mAbs with the lowest ED 50 are those with the highest apparent affinity.

Then the inventors tested the ability of anti-ICOS mAbs to inhibit the binding of ICOS L (a recombinant form of human IgG1 Fc domain) carried by the JICOS.1 cell.

They used a gradient of concentration of anti-ICOS mAbs and they reveled the fixation to ICOS L Fc thanks to a probe coupled to a fluorochrom (GAH-PE: Goat anti-human-PE). The analysis was made by flow cytometry. The inventors thus determined the ID 50 i.e. the dose which inhibits 50% of the binding of ICOS L-Fc on ICOS.

The more the ID 50 is little, the more mAb easily compete with recombinant ICOS Fc.

The inventors thus evidenced that ICOS R 314-8 and ICOS R 53-3 have a high affinity for their binding site (ED 50<0.5 ug/ml) and a significant blocking potential (ID 50<1 mg/ml).

The antibody ICOS R 314-8 was therefore chosen for being coupled to the fluorochrome Alexa Fluor 647 and used in flow cytometry analysis.

2—Anti-ICOS mAbs Differ in their Ability to Induce the Production of IL-10 by Activated CD4+ T Cell The inventors tested the ability of the mAbs to act as agonist antibodies, i.e. being able to have the same action as the natural ligand of ICOS, using functional tests. The studied parameter studied was the secretion of IL-10 since ICOS induces the production of IL-10 by LT.

The agonistic potential of anti-ICOS mAbs were tested on CD4+ T cells, which were pre-activated with CD3/CD28 beads for 48 h and distributed on a plate where anti-CD 3 mAb were coated for continuing the stimulation along with the various anti-ICOS mAbs.

The culture supernatants were then assayed for 48 h for IL-10 and the secretion of IL-10 induced by the different anti-ICOS mAbs was compared based to the secretion of IL-110 induced by a commercially available anti-ICOS mAb (ICOS c)

The anti-ICOS mAbs 53-3, 88-2 and 92-17 significantly increased IL-10 secretion of CD4+ and thus are agonist antibodies. Regarding, anti-ICOS mAbs 145-1 and 314-8, no significant increase in the production of IL-10 was detected.

The inventors finally showed that anti-ICOS mAbs 53-3, 88-2 and 92-17 are better agonists than the commercially available anti-ICOS. Indeed, if one considers the commercially available anti-ICOS mAb as reference, the anti-ICOS mAb 88-2 causes increased secretion of IL-10 of +61%, anti-ICOS mAb 92-17 of +20% and anti-ICOS mAb 53-3 of +14%.

The results are summarized in the following table:

| mAb | Isotype | [ED] 50 (µg/ml) | [ID] 50 (µg/ml) | Agonist effect |
|---|---|---|---|---|
| ICOS 88-2 | IgG1- L | 1.60 | 17 | +++ |
| ICOS 314-8 | IgG1- K | 0.06 | 0.29 | − |

Example 2

Use of an Antagonist Antibody of the Invention and an Agonist Antibody of the Invention Material and Methods Immunohistochemistry Frozen primary breast tumor sections were stained with mouse anti-FOXP3, or anti-Ki67 and revealed using the ImmPRESS anti-mouse Ig peroxidase kit (Abcys, Paris, France) according to the supplier's instructions and DAB. Then, the second primary antibody (mouse anti-ICOS (53.3), anti-CD3, anti-BDCA2 was added and revealed with ImmPRESS kit and Histogreen (Abcys). The specificity of the staining was assessed using mouse isotype controls in place of the first or the second primary antibody.

Purification of Mononuclear Cells from Breast Tumors, Tonsils and Healthy Blood

Mononuclear cells (MNC) were purified, from healthy peripheral blood obtained from EFS or from enzymatic dilaceration of primary breast tumors or tonsils samples, by Ficoll density gradient centrifugation.

Phenotypic Analysis of pDC and T Cells Subsets

For extensive phenotypic analysis, pDC were identified among total MNC as $CD4^+CD123^+$ cells using FITC or PE anti-CD123 and PE-Cy5 anti-CD4 and PE-coupled antibodies against CD40, CD86 or ICOSL. T cells were identified as $CD3^+CD4^+$ cells. Treg were identified either by the multi color phenotype $CD4^+$ $CD127^-$ $CD25^{high}$ or for their FoxP3 expression after gating on $CD3^+CD4^+$ T cells.

Proliferation of Ta-Treg and Ta-Tconv or their blood counterpart was assessed by multicolor analysis allowing Treg $CD4^+$ ($CD127^-$ $CD25^{high}$) and Tconv ($CD4^+CD127^+$ $CD25^{Low/-}$) characterization associated with KI67 Ab staining.

Flow cytometric analysis was performed on a FACScan (BD Biosciences) or an ADP Cyan (Beckman Coulter) and data were analyzed with Cell Quest Pro software (BD Biosciences) or FlowJo (Treestar).

Purification of pDC pDC were purified from lineage(Lin)-negative enriched MNC by either magnetically activated cell sorting using CD304/BDCA-4 microbeads kit or negative depletion using pDC isolation kit (Miltenyi Biotec)) or FACS®-sorting (FACSVantage SE™ DiVa flow cytometer, BD Biosciences) as $Lin^-CD4^+CD11c^-$ cells. Purity was routinely >98%.

In Vitro Generation of Monocytes Derived DC (MoDC)

MoDC were obtained from blood purified monocytes after 7 days differentiation in GM-CSF (100 ng/ml)+IL-4 (50 UI/ml) (Schering Plough, Kenilworth USA).

$CD4^+$ Memory T Cells and Treg Purification

Memory $CD4^+$ T cells (>95% purity) were obtained from MNC after magnetic depletion including anti-CD45RA Ab, as described (Gobert et al, 2009). $CD4^+CD25^{high}CD127^-$ Treg and $CD4^+CD25^-CD127^{low/-}$ conventional $CD4^+$ T cells were FACS®-sorted from purified memory $CD4^+$ T cells (Purity>98%).

To follow their in vitro proliferation, purified memory CD4+ T cells were stained at day 0 with CFSE. Viable cells were selected by DAPI exclusion or Live and Dead reagent in case of cell permeabilisation (200,000 and 5,000 minimum events were gated on the total cell population and on purified cells respectively).

DC-T Cell Co-Cultures

Allogeneic memory CD4+ T cells, Treg or CD4+ Tconv cells were cultured at $3\times10^4$ to $5\times10^4$ cells in complete medium with IL-2 (100 IU/ml) and highly purified TApDC, healthy pDC or MoDC that were pre-activated for 24 h with IL-3, GM-CSF (10 ng/ml) in the presence of R848. Addition of T lymphocytes on pre-activated DC subsets was done in triplicate in 96-well round-bottomed plates at a ratio of 1:5 (DC/T cells) and co-cultured for 5 days. Proliferation was assessed either by CFSE dilution in experiments analysing FoxP3 expression or by DNA synthesis analyzed by $^3$H-TdR uptake.

The impact of ICOS/ICOSL engagement was assessed by addition of ctrl Ab, commercial (ISA-3) or proprietary (314.8) anti ICOS Ab or anti ICOSL (MIH12) in the cultures. To assess T cell cytokines secretion by ELISA, cells were co-cultured with pDC or TApDC, and supernatants harvested at day 5 were centrifuged and stored at $-20°$ C.

Stimulation of Tconv and Treg with Artificial Beads

Artificial APC were produced as described in example 1. Treg ($3\times10^4$) or Tconv ($1\times10^5$) sorted from tonsil or Ta-CD4+ T cells ($1\times10^5$) purified from tumors were cultured for 5 days with artificial beads at a ratio 1:1 (artificial APC:T cell) in the presence of IL-2 (100 UI/ml) in 96 U-bottomed wells under 2000. Proliferation was assessed either by CFSE dilution or by DNA synthesis analyzed by $^3$H-TdR uptake.

Cytokines Detection in T Cell Cultures Supernatants by ELISA

IL-10, IFNγ and IL-2 in 5 days culture supernatants were quantified by ELISA using commercial kits from Bender Medsystems according to manufacturer's instructions.

Result

The data presented below are intended to analyze the impact of two antibodies against ICOS (i.e. blocking MAb 314.8; agonist MAb 88.2) developed by the inventors in order to validate
i) the blockade of ICOS by antagonistic 314.8 MAb as a new promising drug candidate to abrogate the immunosuppressive response observed in breast cancer; and
ii) the engagement of ICOS by the agonist 88.2 MAb on CD4+ T cells to favour the amplification of Treg that would be of interest in the field of autoimmunity.

Ta-Treg that Highly Express ICOS are Present within Lymphoid Aggregates in Primary Breast Tumors and Proliferate In Situ The inventors have previously demonstrated the presence of Tumor associated regulatory T cells (Ta-Treg) expressing $CD25^{high}$ and FoxP3 in primary breast tumors within lymphoid aggregates correlating with a poor prognosis and increased risk of metastasis (Gobert et al., 2009). These Ta-Treg represent 15% to 25% of total CD4+ TaT cells, are highly activated as they express ICOS, CD39, GITR and HLA-DR and suppress TaTconv proliferation and cytokines secretion (IL-2, IFNγ).

These Ta-Treg proliferate within the primary breast tumor environment in situ (Gobert et al., 2009) as demonstrated by either the presence of ICOS Treg co-expressing Ki67 on tumor frozen sections, (FIG. 1A) or the higher proportion of KI67+ cells within purified Ta-Treg and Treg from blood (respectively 8% and 4%) compared to Ta-Tconv and Tconv (3% and 0.3% respectively) (FIG. 1B).

In contrast with these in vivo results, the inventors demonstrated that in vitro stimulation of purified Ta-Treg with expand beads (beads coated with agonist anti CD3 and anti CD28) is not capable to favor Ta-Treg amplification in contrast to that observed with purified TaTconv or purified Treg or Tconv from blood of healthy donors (FIG. 1C).

The inventors hypothesized that the ICOS engagement is essential for Ta-Treg proliferation and functions.

A) Use of an Antagonist Antibody of the Invention

Blockade of ICOS/ICOS-L Interaction Through Antagonist ICOS mAb (314.8) Ta-Treg Interact In Situ with Ta pDC within Lymphoid Aggregates in Primary Breast Carcinoma Several studies reported the expression of ICOS-L, the specific ligand of ICOS, on pDC (Janke et al., 2006). Using immuno-histochemistry on tumor frozen sections, the inventors observed that Ta-CD3+ T cell present within the lymphoid aggregates surrounding the tumor are in interaction with Ta-pDC BDCA2+ (FIGS. 1D and 1E). A double staining with FoxP3 and BDCA2 Ab revealed that Ta-Treg are in close contact with Ta-pDC in these lymphoid aggregates, suggesting that this interaction will favor the ICOS engagement by ICOS-L in tumors (FIG. 1F).

Ta-pDC are Activated but Did not Express ICOS-L as a Potential Consequence of In Situ ICOS/ICOS-L Interaction After purification from tumor disaggregation, Ta-pDC show an activated phenotype as they express up regulated levels of CD86 and CD40 compared to healthy blood and matched patient's blood pDC. As reported by several groups (Ito et al., 2007; Janke et al., 2006), freshly isolated healthy blood pDC express low levels of ICOS-L that is strongly unregulated after IL-3 exposure or TLR7/8 ligation, which is not observed on other DC subsets (mDC, MoDC). Interestingly, contrasting with their activated status ($CD86^+CD40^+$), Ta-pDC are devoid of membrane ICOS-L expression. In contrast freshly isolated paired patients' blood pDC or healthy blood pDC express ICOS-L. After a 24 h culture period in IL-3 or upon TLR7/8 ligation, sorted Ta-pDC reacquire a strong ICOS-L expression demonstrating their ability to modulate this ICOS-L expression (data not shown). Among CD3+ TaT cells, ICOS is strongly expressed on Ta-Treg (69.9% MFI: 361) in contrast to TaTconv (23% MFI: 83) or TaCD8+ (2% MFI: 50). These results indicate that in situ ICOS/ICOS-L interaction leads to ICOS-L down regulation on Ta-pDC membrane.

Blockade of ICOS/ICOS-L Interaction Through Antagonistic Anti ICOS MAb (314.8) Abrogate ICOS-L Downregulation on pDC To test this hypothesis, healthy blood T cells were cultured with TLR7-activated pDC purified from tonsil. The inventors observed after 24 h culture period with increased T:pDC ratio α dose dependent ICOS-L downregulation on pDC. Interestingly the addition of our antagonist MAb against ICOS (314.8) abrogates totally this ICOS-L downregulation on pDC, result that is not reproduced using commercial anti ICOS antibody (ISA-3) (data not shown).

The results demonstrate Ta-pDC and Ta-Treg interactions through ICOS/ICOS-L and indicate that ICOS ligation could be involved in Ta-Treg activation and proliferation.

Coculture of CD4+ T Cells as Well as Purified Treg with Activated pDC but not MoDC Induced Treg Proliferation that is Blocked with 314.8

To test the ability of ICOS/ICOS-L interactions to induce Treg amplification, the inventors cultured total memory CD4+ T cell with healthy blood purified allogeneic TLR7/8 (R848)-activated pDC or mDC. Among purified CD4+ T cells, 3.5% expressed FoxP3 (data not shown). After 5 days of co-culture with pDC the proportion of $FoxP3^{high}$ expressing cells, corresponding to Treg, rises to 12.3% and the addition of 314.8 Ab blocks by 80% this enrichment in FoxP3$^{high}$ cells. In contrast, coculture of CD4$^+$ T cell with activated mDC was not able to favor a distinct FoxP3$^{high}$ subpopulation among CD4$^+$ T cells, and the addition of 314.8 has no significant effect (6.3% to 8%).

Similar results were obtained with CD4$^+$ T cells purified from tumor. Ta-Treg Foxp3$^+$ represent 9% of freshly purified CD4$^+$ TaT cells (data not shown). Their co-culture with R848 activated pDC increases the proportion of Ta-Treg to 14.5% whereas the addition of 314.8 leads to a decrease of Ta-Treg proportion to 4.5%, below the starting level.

FACS sorted purified Treg or Tconv populations stained with CFSE were cultured with R848-activated pDC or LPS-activated MoDC to analyze their proliferation capacity by flow cytometry (dilution of CFSE expression). First, the inventors observed that in absence of exogenous IL-2, that activated MoDC do not induce purified Treg proliferation whereas Tconv strongly proliferate. In contrast coculture with activated pDC is able to induce a strong proliferation of both purified Treg and Tconv.

The addition of anti-ICOS 314.8 MAb strongly reduces Treg and Tconv proliferation when pDC are used as APC whereas Tconv proliferation is unchanged in cocultures with MoDC. In this experiment, ICOS or ICOS-L blockade with commercial antibodies (ISA-3 mAb or MIH-12 MAb) do not affect neither Treg nor Tconv proliferation in pDC/T co-cultures.

These data demonstrate that the anti-ICOS 314.8 MAb neutralizes ICOS engagement on Treg and abrogates their expansion induced by pDC.

ICOS and ICOS-L Blockade Abrogate IL-10 Secretion During pDC Mediated T Cell Activation without Interfering Strongly on MoDC/T Co-Culture.

314.8 MAb also reduces Tconv proliferation in response to activated pDC stimulation. The inventors determined the impact of 314.8 on IFNγ and IL-10 secretion by Elisa during Tconv and allogeneic R848 activated pDC (FIG. 2A) or and LPS activated MoDC (FIG. 2B) co-cultures. In these settings IL-10 secretion is totally abrogated by 314.8 mAb (217+/−31 pg/ml in control and 13+/−6 pg/ml with 314.8). Whereas, the IFNγ secretion is slightly reduced upon the addition of 314.8 MAb on co-cultures with pDC (32% reduction 507+/−53 pg/ml in control condition and 341+/−73 pg/ml with 314.8) (FIG. 2A). In Tconv/MoDC co-cultures ICOS inhibition leads to slightly increased secretions of IL-10 and IFNγ (FIG. 2B).

B) Use of an Agonist Antibody According to the Invention

Use of agonist anti ICOS MAb (88.2) to mimic ICOS engagement

To perfect their understanding on ICOS functions on Treg and Tconv, the inventors generated a model of artificial APC using beads coated with agonist MAbs leading to CD3 (OKT3); CD28 (CD28.2) and/or ICOS (88.2, Table 1) signaling on purified T cells.

ICOS Engagement with an Agonist MAb (88.2) on Treg Induced their Proliferation and Their Capacity to Secrete High Amounts of IL-10

First the inventors observed that Treg from healthy donors proliferate in response to anti CD3/88.2 beads in presence of exogenous IL-2 (FIG. 3A). As previously reported (Simpson et al., 2010; Ito et al., 2008) upon activation through TCR and ICOS engagement in presence of IL-2, both purified Tconv and Treg subpopulations secrete high amounts of IL-10 (311+/−22 pg/ml and 426+/−48 pg/ml respectively) and low levels of IFNγ (205+/−8 pg/ml and 381+/−12 pg/ml). This result contrasts with data obtained using the anti CD3/anti CD28 beads. In this model Tconv secrete large amounts of IFNγ (1213+/−72 pg/ml) and low levels of IL-10 (69+/−58 pg/ml) whereas Treg secrete IL-10 and low levels of IFNγ (422+/−36 pg/ml and 305+/−31 pg/ml respectively) (FIG. 3B).

Similar experiments with T cells purified from tumor demonstrated that CD4$^+$ TaT cells produce similar levels of IL-10 in response to ICOS and CD28 while the levels of IFNγ are weaker in response to ICOS compared to CD28 engagement (FIG. 3C).

ICOS Engagement Blocks CD28-Induced IL-2 and Consequently Reduces Proliferation and IFNγ Secretion Whereas, CD4$^+$ memory T cells proliferate in response to anti CD3/anti CD28 stimulation independently of exogenous IL-2, no proliferation is observed in response to anti CD3/88.2 stimulation (FIG. 4A). The addition of hIL-2 rescues this proliferation in a dose dependent manner. Interestingly, the co-engagement of ICOS and CD28 in the absence of IL-2 reduces significantly the proliferation of CD4$^+$ memory T cells compared to only CD28 engagement, and this is completely rescued in the presence of 100 UI/ml IL-2. Interestingly, ICOS ligation through 88.2 mAb abrogates IL-2 secretion detected with anti CD3/anti CD28 stimulation (FIG. 4B). Taken together, this argues in favor of a reduced spontaneous IL-2 secretion when ICOS and CD28 are co-engaged compared to the only CD28 engagement suggesting an ICOS inhibitory function on CD28-induced IL-2 secretion.

Moreover, even in the presence of exogenous IL-2, the inventors observed a 50% reduction of IFNγ produced by Tconv, when ICOS and CD28 are triggered compared with anti CD3/anti CD28 beads (FIG. 4C).

In contrast, whereas IL-10 secretion is strictly IL-2 dependent when cells are activated under ICOS triggering, as previously described (Ito 2008, Paulos 2010), the addition of ICOS signal does not affect the IL-10 secretion induced by anti CD3/anti CD28 (FIG. 4C).

All together these results demonstrate that ICOS ligation reduced the ability of anti CD3/anti CD28 to favor Th1 polarisation (through the reduced IFNγ production) but sustains the IL-10 production favoring the development of an immunosuppressive environment.

ICOS Engagement Through 88.2 MAb Increased the Treg Suppressive Function

To assess that ICOS engagement can be associated with an immunosuppressive T cell response, the inventors setup suppressions assays in the absence of exogenous IL-2 to compare anti CD3/anti CD28/IgG and anti CD3/anti CD28/88.2 beads efficiency. The addition of the ICOS signaling (88.2) strongly increases the suppressive function of Treg compared with the anti CD3/anti CD28/IgG1 (51% inhibition in condition one Treg for 4 Tconv anti CD3/anti CD28/88.2 compared to 21% inhibition with anti CD3/anti CD28/IgG). All together these results demonstrate that ICOS engagement favors an immunosuppressive T cell response that could result either from an increased Tconv sensitivity to suppression or a stronger Treg suppressive ability.

Example 3

Analysis of Prognostic Impact of Detection of ICOS$^+$ Treg Cells within Primary Breast Tumors 120 paraffin embedded primary tumor samples with 10 years clinical follow up were tested for their expression of ICOS using a commercial anti ICOS rabbit polyclonal Ab (Spring Biosciences). ICOS$^+$ cells were quantified in double blind on 6 different replicates for each tumor and mean of the results were compiled (data not shown). To perform the statistical analysis the inventors used the median as cut-off to have equilibrated groups.

In univariate analysis the inventors demonstrate that the presence of ICOS$^+$ cells (>1.66 ICOS$^+$ cells/spot) correlated with high tumor grade (p=0.007), expression of Estrogen receptor by tumor cells (p=0.018), luminal A/B molecular subtypes (p<0.001) and absence of Her2/neu overexpression (p=0.035).

The impact of ICOS$^+$ cells detection within primary breast tumors on overall survival (OS) or progression free survival (PFS) was investigated.

Whereas 6/59 deaths were observed in the ICOS– group, 14/61 patients deceased in the ICOS$^+$ demonstrating the significant prognostic value of ICOS$^+$ detection on OS (Log Rank test p value=0.0465) (FIG. 9A). Similar analysis performed on PFS demonstrated ICOS$^+$ cells was associated with a poorer overall survival, with progression in 11/59 in ICOS$^-$ group, whereas 20/61 patients progressed in the ICOS$^+$ group (p=0.0285) (FIG. 9B).

Example 4

Confirmation of the Existence of In Situ Interaction of pDC with ICOS$^+$ Treg in the Tumor Environment Ex vivo co-culture of tumor cell dilacerations in the presence of anti ICOS 314.8 MAb or Ctrl Ab for 48 h in presence of IL-3 (20 ng/ml). At the end of the culture period, the expression of ICOS-L on pDC is observed only in the presence of the anti ICOS 314.8 MAb and not with control Ab, demonstrating that the down regulation of ICOS-L on pDC is mediated through an interaction with ICOS$^+$ cells (data not shown).

Example 5

Epithelial Breast Tumor Cells from Either Established Cell Lines or Fresh Tumor Samples do not Express ICOS-L in Contrast to Melanoma or Glioma Tumor Cells Even after Ex Vivo Culture with Anti ICOS Antibody 314.8

Breast epithelial tumor cells lines were harvested in PBS EDTA to avoid trypsin-associated degradation of the Ag and cells were stained with anti ICOS-L antibody to evaluate the expression at cell surface by flow cytometry. None of the cell lines tested was found positive for ICOS-L (FIG. 5A). Similar analyses were performed on 48 h cultured primary tumor disaggregations in presence of anti ICOS Ab (314.8) or control Ab plus IL-3 (20 ng/ml) (FIG. 5B).

Example 6

Impact of a Surrogate Rat Anti-Mouse Anti ICOS Ab (17G9, IgG2b) on Mammary Tumor Growth in a Syngenic Mammary Tumor Model Mouse mammary tumor model was obtained in female FVB mice in 28-35 days after orthotopic injection of the Neu 15 cell line. The generated tumors appear significantly infiltrated by activated Ta-pDC, ICOS$^{high}$ TATreg and resting TATconv.

Injection of 17G9 antibody (50 µg/ml) intra-peritoneally three times a week from day 11 after tumor implantation results in a reduced Neu15 tumor size at late time points compared to the injection of control Ab (LTF2, IgG2b) (p=0.053) (FIG. 6).

Example 7

A: Treg Cells Numbers are Increased within Primary Cervix Cancer

Figure 7:
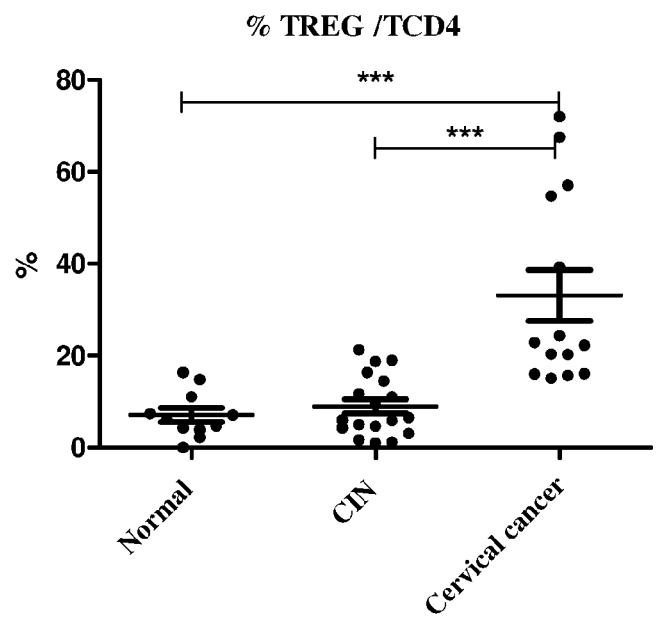
Figure 7:
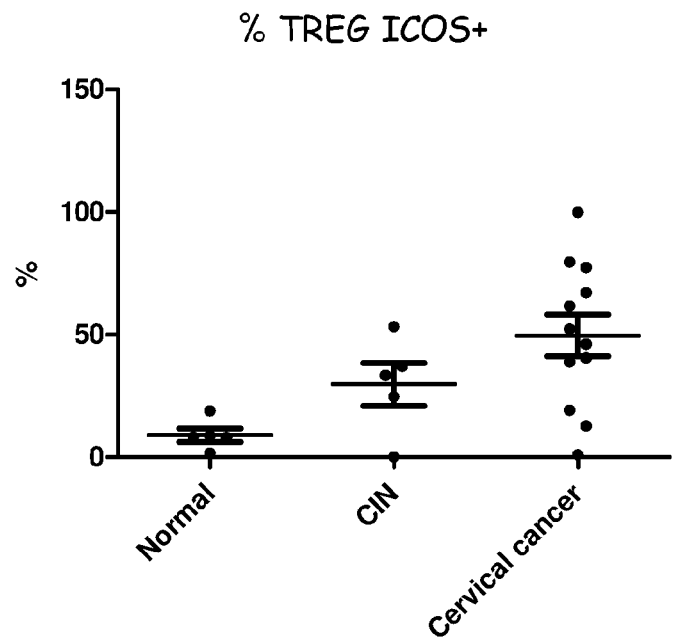

Cervical samples were obtained from patients either with dysplasia (CIN2/3, n=18) or cancer (n=14). Normal cervical tissue was used as control (n=11). Samples were obtained by both enzymatic and physical dissociations. After washing, mononuclear cells were incubated with labeled mAbs and Tregs enumerated as CD127$^{low}$CD25$^{bright}$CD4$^+$ T cells. The percentage of Treg within the CD4$^+$ subset is depicted. Treg were increased within cervical cancer samples in comparison to normal tissue and dysplasia. Hence, this increase is associated to the cancer development (FIG. 7A).

B: Treg Cells ICOS$^+$ are Increased within Primary Cervix Cancer

Cervical samples were obtained from patients either dysplasia (CIN2/3, n=5) or cancer (n=12). Normal cervical tissue was used as control (n=5). Samples were obtained by both enzymatic and physical dissociation. After washing mononuclear cells were incubated with labeled using ICOS mAbs and Tregs enumerated. The percentage of Treg ICOS within the CD4$^+$ subset is depicted ICOS$^+$ Treg are present within tissues with only a trend to their increase in cervical cancer due the limited numbers of samples analyzed (FIG. 7B).

Example 8

Increase of ICOS Expressing Treg in Non Hodgkin Lymphoma (NHL)

The inventors have analyzed the Teg numbers and the expression of ICOS on Treg in LNH samples. Fresh lymphoma cells teased from lymph nodes were collected from 45 patients with informed consent. Lymphoma samples correspond to Hodgkin disease (HD, n=11), follicular lymphoma (FL, n=13), diffuse large B cell lymphoma (DLBCL, n=10), mantle cell lymphoma (MCL, n=5) and marginal zone lymphoma (MZL, n=6). Detection of Treg cells was performed by incubation for 20 min at 4° C. with anti-ICOS-PE (Becton Dickinson™), anti-CD3-ECD, anti-CD4-Pacific Blue (Beckman Coulter®), anti-CD127 FITC, anti-CD25 APC-Cy7 and LIVE/DEAD® Fixable Dead Cell Stain Kit (Invitrogen™). After staining, each cell preparation was washed twice in PBS, fixed with 2% paraformaldehyde and analyzed on a FACS LSR2 flow cytometer (Becton Dickinson™). Data were analyzed using FlowJo Software (TreeStar™). Treg were increased in all lymphoma samples except HD. Most of Treg displayed an increased expression of ICOS in comparison to control lymph nodes (FIG. 8).

Example 9

Sequencing of Icos 314.8 (CNCM I-4180)

Total RNA was extracted from provided frozen hybridoma cells and cDNA was synthesized. Then, RT-PCR was performed to amplify the variable regions (heavy and light chains) of the MAb. The MAb variable regions of the heavy and light chains were cloned into a cloning vector separately, then the obtained sequences were analyzed to deduce the sequences of the MAb.

Materials

Hybridoma cells ICOS 314.8 (CNCM I-4180); TRIzol® Plus RNA Purification System (Invitrogen, Cat. No: 15596-026); SuperScript™ III First-Strand Synthesis System (Invitrogen, Cat. No: 18080-051).

Methods

Total RNA Extraction

Total RNA was isolated from the hybridoma cells according to the technical manual of TRIzol® Plus RNA Purification System. The total RNA was checked by gel electrophoresis.

RT-PCR

Total RNA was reverse transcribed into cDNA using isotype specific anti-sense primer or universal primer and whole procedure was according to the technical manual of SuperScript™ III First-Strand Synthesis System. The antibody fragment will be amplified according to the standard operation protocol of RACE method of GenScript.

Cloning of Antibody Genes

Target PCR products of antibody genes were cloned into the cloning vector separately according to standard molecular cloning procedures.

Screening and Sequencing

Colony screening was employed to screen clones with inserts of correct sizes, and no less than ten independent positive colonies were sequenced for each antibody fragment.

Results and Analysis

Total RNA Extraction

Total RNA of the sample was run alongside of DL3000 DNA marker on a 1.5% agarose/GelRed™ gel electrophoresis.

PCR Product of Antibody Genes

4 μl PCR products of each sample were run alongside of DL3000 DNA marker on a 1.5% agarose/GelRed™ gel electrophoresis.

Sequencing Results and Analysis

The sequencing results are as follows. The consensus DNA sequences and corresponding amino acid sequences are listed below:

```
Heavy chain: DNA sequence (426 bp): Leader sequence-FR1-CDR1-FR2-
CDR2-FR3-CDR3-FR4
                                                     (SEQ ID NO: 13)
ATGGGATGGCGCTGTATCATCCTCTTCTTGGTATCAACAGCTACAGGTGTCCACTCCCAGGTCC

AACTACAGCAGCCTGGGACTGAACTTATGAAGCCTGGGGCTTCAGTGAAGCTGTCCTGCAAGGC

TTCTGGCTACACCTTCACCACCTACTGGATGCACTGGGTGAAGCAGAGGCCTGGACAAGGCCTT

GAGTGGATCGGAGAGATTGATCCTTCTGATAGTTATGTTAACTACAATCAAAACTTTAAGGGCA

AGGCCACATTGACTGTAGACAAATCCTCCAGCACAGCCTACATACAGCTCAGCAGCCTGACATC

TGAGGACTCTGCGGTCTATTTTTGTGCGAGATCCCCTGATTACTACGGTACTAGTCTTGCCTGG

TTTGATTACTGGGGCCAAGGGACTCTGGTCACTGTCTCTACA

Heavy chain: Amino acids sequence (142 AA): Leader sequence-FR1-
CDR1-FR2-CDR2-FR3-CDR3-FR4
                                                     (SEQ ID NO: 14)
MGWRCIILFLVSTATGVHSQVQLQQPGTELYKPGASVKLSCKASGYTFTTYWMHWVKQRPGQGL

EWIGEIDPSDSYVNYNQNFKGKATLTVDKSSSTAYIQLSSLTSEDSAVYFCARSPDYYGTSLAW

FDYWGQGTLVTVST

Light chain: DNA sequence (396 bp): Leader sequence-FR1-CDR1-FR2-
CDR2-FR3-CDR3-FR4
                                                     (SEQ ID NO: 15)
ATGAGGTGCCTAGCTGAGTTCCTGGGGCTGCTTGTGCTCTGGATCCCTGGAGTCATTGGGATA

TTGIGATGACTCAGGCTGCACCCTCTGTACCTGTCACTCCTGGAGAGTCAGTATCCATCTCCTG

CAGGTCTAGTAAGAGTCCCCTGCATAGTAACGGCAACATTTACTTATATTGGTTCCTGCAGAGG

CCAGGCCAGTCTCCTCAGCTCCTGATATATCGGATGTCCAACCTTGCCTCAGGAGTCCCAGACA

GGTTCAGTGGCACTGGGTCAGGAACTACTTCACACTGAAAATCAGTAGAGTGGAGGCTGAGGA

TGTGGGTGTTTATTACTGTATGCAACATCTAGAATATCCGTACACGTTCGGAGGGGGGACCAAG

CTGGAAATAAAA

Light chain: Amino acids sequence (132 AA): Leader sequence-FR1-
CDR1-FR2-CDR2-FR3-CDR3-FR4
                                                     (SEQ ID NO: 16)
MRCLAEFLGLLVLWIPGVIGDIVMTQAAPSVPVTPGESVSISCRSSKSPLHSNGNIYLYWFLQR

PGQSPQLLIYRMSNLASGVPDRFSGSGSGTTFTLKISRVEAEDVGVYYCMQHLEYPYTFGGGTK

LEIK
```

Thus, sequences of ICOS 314.8 (CNCM I-4180) can be resumed as follows:

|        | DNA sequence | Aminoacid sequence |
|--------|--------------|---------------------|
| H-CDR1 | GGCTACACCTTCACCACCTAC TGGATGCAC (SEQ ID NO: 1) | GYTFTTYWMH (SEQ ID NO: 7) |
| H-CDR2 | GAGATTGATCCTTCTGATAGTT ATGTTAACTACAATCAAAACTT TAAGGGC (SEQ ID NO: 2) | EIDPSDSYVNYNQNFKG (SEQ ID NO: 8) |
| H-CDR3 | TTTGATTAC (SEQ ID NO: 3) | FDY (SEQ ID NO: 9) |
| L-CDR1 | AGGTCTAGTAAGAGTCCCCTGC ATAGTAACGGCAACATTTACTT ATAT (SEQ ID NO: 4) | RSSKSPLHSNGNIYLY (SEQ ID NO: 10) |
| L-CDR2 | CGGATGTCCAACCTTGCCTCA (SEQ ID NO: 5) | RMSNLAS (SEQ ID NO: 11) |
| L-CDR3 | ATGCAACATCTAGAATATCCGT ACACG (SEQ ID NO: 6) | MQHLEYPYT (SEQ ID NO: 12) |

Example 10

Sequencing of Icos 88.2 (CNCM I-4177)

Total RNA was extracted from provided frozen hybridoma cells and cDNA was synthesized. Then, RT-PCR was performed to amplify the variable regions (heavy and light chains) of the MAb. The MAb variable regions of the heavy and light chains were cloned into a cloning vector separately, then the obtained sequences were analyzed to deduce the sequences of the MAb.

Materials
Hybridoma cells ICOS 88.2 (CNCM I-4177); TRIzol® Plus RNA Purification System (Invitrogen, Cat. No: 15596-026); SuperScript™ III First-Strand Synthesis System (Invitrogen, Cat. No: 18080-051).

Methods

Total RNA Extraction
Total RNA was isolated from the hybridoma cells according to the technical manual of TRIzol® Plus RNA Purification System. The total RNA was checked by gel electrophoresis.

RT-PCR
Total RNA was reverse transcribed into cDNA using isotype specific anti-sense primer or universal primer and whole procedure was according to the technical manual of SuperScript™ III First-Strand Synthesis System. The antibody fragment will be amplified according to the standard operation protocol of RACE method of GenScript.

Cloning of Antibody Genes
Target PCR products of antibody genes were cloned into the cloning vector separately according to standard molecular cloning procedures.

Screening and Sequencing
Colony screening was employed to screen clones with inserts of correct sizes, and no less than ten independent positive colonies were sequenced for each antibody fragment.

Results and Analysis

Total RNA Extraction
Total RNA of the sample was run alongside of DL3000 DNA marker on a 1.5% agarose/GelRed™ gel electrophoresis.

PCR Product of Antibody Genes
4 μl PCR products of each sample were run alongside of DL3000 DNA marker on a 1.5% agarose/GelRed™ gel electrophoresis.

Sequencing Results and Analysis
The sequencing results are as follows. The consensus DNA sequences and corresponding amino acid sequences are listed below:

Heavy chain: DNA sequence (429 bp): Leader sequence-FR1-<u>CDR1</u>-FR2-<u>CDR2</u>-FR3-<u>CDR3</u>-FR4
(SEQ ID NO: 29)
ATGGGATGGAGCTGTATCATCCTCTTCTTGGTAGCAACAGCTACAGGTGTCCACTCCCAGGTCC

AACTGCAGCAGCCTGGGGCTGAGCTGGTGAGGCCTGGGGCTTCAGTGAAGCTGTCCTGCAAGGC

TTCT<u>GGCTACAGTTTCACCAGCTACTGGATAAAC</u>TGGGTGAAGCAGAGGCCTGGACAAGGCCTT

GAGTGGATCGGA<u>AATATTTATCCTTCTGATAGTTATACTAACTACAATCAAATGTTCAAGGAC</u>A

AGGCCACATTGACTGTAGACAAATCCTCCAACACAGCCTACATGCAGCTCACCAGCCCGACATC

TGAGGACTCTGCGGTCTATTACTGTACAAGA<u>TGGAATCTTTCTTATTACTTCGATAATAACTAC</u>

<u>TACTTGGACTAC</u>TGGGGCCAAGGCACCACTCTCACAGTCTCCTCA

Heavy chain: Amino acids sequence (143 AA): Leader sequence-FR1-<u>CDR1</u>-FR2-<u>CDR2</u>-FR3-<u>CDR3</u>-FR4
(SEQ ID NO: 30)
MGWSCIILFLVATATGVHSQVQLQQPGAELVRPGASVKLSCKAS<u>GYSFTSYWIN</u>WVKQRPGQGL EWIG<u>NIYPSDSYTNYNQMFKD</u>KATLTVDKSSNTAYMQLTSPTSEDSAVYYCTR<u>WNLSYYFDNNY</u>

<u>YLDY</u>WGQGTTLTVSS

Light chain: DNA sequence (396 bp): Leader sequence-FR1-<u>CDR1</u>-FR2-<u>CDR2</u>-FR3-<u>CDR3</u>-FR4
(SEQ ID NO: 31)
ATGAGGTGCCTAGCTGAGTTCCTGGGGCTGCTTGTGCTCTGGATCCCTGGAGCCATTGGGGATA

TTGTGATGACTCAGGCTGCACCCTCTGTACCTGTCACTCCTGGAGAGTCAGTATCCATCTCCTG

```
CAGGTCTAGTAAGAGTCTCCTGCATAGTAATGGCAACACTTACTTGTATTGGTTCCTGCAGAGG

CCAGGCCAGTCTCCTCAACTCCTGATATATCGGATGTCCAACCTTGCCTCAGGAGTCCCAGACA

GGTTCAGTGGCAGTGGGTCAGGAACTCCTTTCACACTGAGAATCAGTAGAGTGGAGGCTGAGGA

TGTGGGTGTTTATTACTGTATGCAACATCTAGAATATCCGTGGACGTTCGGTGGAGGCACCAAG

CTGGAAATCAAA
```

Light chain: Amino acids sequence (132 AA): Leader sequence-FR1-CDR1-FR2-CDR2-FR3-CDR3-FR4
(SEQ ID NO: 32)

MRCLAEFLGLLVLWIPGAIGDIVMTQAAPSVPVTPGESVSISCRSSKSLLHSNGNTYLYWFLQR

PGQSPQLLIYRMSNLASGVPDRFSGSGSGTAFTLRISRVEAEDVGVYYCMQHLEYPWTFGGGTK

LEIK

Thus, sequences of ICOS 88.2 (CNCM I-4177) can be resumed as follows:

| | DNA sequence | Aminoacid sequence |
|---|---|---|
| H-CDR1 | GGCTACAGTTTCACCAGCTACTGGATAAAC (SEQ ID NO: 17) | GYSFTSYWIN (SEQ ID NO: 23) |
| H-CDR2 | AATATTTATCCTTCTGATAGTTATACTAACTACAATCAAATGTTCAAGGAC (SEQ ID NO: 18) | NIYPSDSYTNYNQMFKD (SEQ ID NO: 24) |
| H-CDR3 | TGGAATCTTTCTTATTACTTCGATAATAACTACTACTTGGACTAC (SEQ ID NO: 19) | WNLSYYFDNNYYLDY (SEQ ID NO: 25) |
| L-CDR1 | AGGTCTAGTAAGAGTCTCCTGCATAGTAATGGCAACACTTACTTGTAT (SEQ ID NO: 20) | RSSKSLLHSNGNTYLYAT (SEQ ID NO: 26) |
| L-CDR2 | CGGATGTCCAACCTTGCCTCA (SEQ ID NO: 21) | RMSNLAS (SEQ ID NO: 27) |
| L-CDR3 | ATGCAACATCTAGAATATCCGTGGACG (SEQ ID NO: 22) | MQHLEYPWT (SEQ ID NO: 28) |

The invention claimed is:

1. An antibody directed against Inducible T-cell costimulatory (ICOS), wherein said antibody has the following 6 CDRs:

(SEQ ID NO: 7, H-CDR1)
GYTFTTYWMH;

(SEQ ID NO: 8, H-CDR2)
EIDPSDSYVNYNQNFKG;

(SEQ ID NO: 9, H-CDR3)
FDY;

(SEQ ID NO: 10, L-CDR1)
RSSKSPLHSNGNIYLY;

(SEQ ID NO: 11, L-CDR2)
RMSNLAS;

(SEQ ID NO: 12, L-CDR3)
MQHLEYPYT.

2. An antibody according to claim 1, wherein the nucleotide sequences encoding the 6 CDRs are:

(SEQ ID NO: 1, H-CDR1)
GGCTACACCTTCACCACCTACTGGATGCAC;

(SEQ ID NO: 2, H-CDR2)
GAGATTGATCCTTCTGATAGTTATGTTAACTACAATCAAAACTTTAAGGG
C;

-continued

```
(SEQ ID NO: 3, H-CDR3)
TTTGATTAC;

(SEQ ID NO: 4, L-CDR1)
AGGTCTAGTAAGAGTCCCCTGCATAGTAACGGCAACATTTACTTATAT;

(SEQ ID NO: 5, L-CDR2)
CGGATGTCCAACCTTGCCTCA;

(SEQ ID NO: 6, L-CDR3)
ATGCAACATCTAGAATATCCGTACACG.
```

3. A method of treatment of a patient in need thereof comprising administering to said patient an antibody according to claim 1, wherein said patient has a disease or condition selected from cancers and chronic infections.

4. The method of treatment according to claim 3, wherein said cancer is a selected from human malignant lymphoma, ovarian cancer, cervical cancer and breast cancer.

* * * * *

SEQUENCE LISTING

```
<160> NUMBER OF SEQ ID NOS: 32

<210> SEQ ID NO 1
<211> LENGTH: 30
<212> TYPE: DNA
<213> ORGANISM: Mus musculus

<400> SEQUENCE: 1
ggctacacct tcaccaccta ctggatgcac                                    30

<210> SEQ ID NO 2
<211> LENGTH: 51
<212> TYPE: DNA
<213> ORGANISM: Mus musculus

<400> SEQUENCE: 2
gagattgatc cttctgatag ttatgttaac tacaatcaaa actttaaggg c            51

<210> SEQ ID NO 3
<211> LENGTH: 9
<212> TYPE: DNA
<213> ORGANISM: Mus musculus

<400> SEQUENCE: 3 tttgattac                                                            9

<210> SEQ ID NO 4
<211> LENGTH: 48
<212> TYPE: DNA
```

<213> ORGANISM: Mus musculus

<400> SEQUENCE: 4
aggtctagta agagtcccct gcatagtaac ggcaacattt acttatat          48

<210> SEQ ID NO 5
<211> LENGTH: 21
<212> TYPE: DNA
<213> ORGANISM: Mus musculus

<400> SEQUENCE: 5
cggatgtcca accttgcctc a                                       21

<210> SEQ ID NO 6
<211> LENGTH: 27
<212> TYPE: DNA
<213> ORGANISM: Mus musculus

<400> SEQUENCE: 6
atgcaacatc tagaatatcc gtacacg                                 27

<210> SEQ ID NO 7
<211> LENGTH: 10
<212> TYPE: PRT
<213> ORGANISM: Mus musculus

<400> SEQUENCE: 7

Gly Tyr Thr Phe Thr Thr Tyr Trp Met His
1               5                   10

<210> SEQ ID NO 8
<211> LENGTH: 17
<212> TYPE: PRT
<213> ORGANISM: Mus musculus

<400> SEQUENCE: 8

Glu Ile Asp Pro Ser Asp Ser Tyr Val Asn Tyr Asn Gln Asn Phe Lys
1               5                   10                  15
Gly

<210> SEQ ID NO 9
<211> LENGTH: 3
<212> TYPE: PRT
<213> ORGANISM: Mus musculus

<400> SEQUENCE: 9

Phe Asp Tyr
1

<210> SEQ ID NO 10
<211> LENGTH: 16
<212> TYPE: PRT
<213> ORGANISM: Mus musculus

<400> SEQUENCE: 10

Arg Ser Ser Lys Ser Pro Leu His Ser Asn Gly Asn Ile Tyr Leu Tyr
1               5                   10                  15

<210> SEQ ID NO 11
<211> LENGTH: 7
<212> TYPE: PRT
<213> ORGANISM: Mus musculus

<400> SEQUENCE: 11

Arg Met Ser Asn Leu Ala Ser
1               5

<210> SEQ ID NO 12
<211> LENGTH: 9
<212> TYPE: PRT
<213> ORGANISM: Mus musculus

<400> SEQUENCE: 12

Met Gln His Leu Glu Tyr Pro Tyr Thr
1               5

<210> SEQ ID NO 13
<211> LENGTH: 426
<212> TYPE: DNA
<213> ORGANISM: Mus musculus

<400> SEQUENCE: 13

| | | | | | |
|---|---|---|---|---|---|
| atgggatggc | gctgtatcat | cctcttcttg | gtatcaacag | ctacaggtgt | ccactcccag | 60 |
| gtccaactac | agcagcctgg | gactgaactt | atgaagcctg | gggcttcagt | gaagctgtcc | 120 |
| tgcaaggctt | ctggctacac | cttcaccacc | tactggatgc | actgggtgaa | gcagaggcct | 180 |
| ggacaaggcc | ttgagtggat | cggagagatt | gatccttctg | atagttatgt | taactacaat | 240 |
| caaaacttta | agggcaaggc | cacattgact | gtagacaaat | cctccagcac | agcctacata | 300 |
| cagctcagca | gcctgacatc | tgaggactct | gcggtctatt | tttgtgcgag | atcccctgat | 360 |
| tactacggta | ctagtcttgc | ctggtttgat | tactggggcc | aagggactct | ggtcactgtc | 420 |
| tctaca | | | | | | 426 |

<210> SEQ ID NO 14
<211> LENGTH: 142
<212> TYPE: PRT
<213> ORGANISM: Mus musculus

<400> SEQUENCE: 14

Met Gly Trp Arg Cys Ile Ile Leu Phe Leu Val Ser Thr Ala Thr Gly
1               5                   10                  15

Val His Ser Gln Val Gln Leu Gln Gln Pro Gly Thr Glu Leu Met Lys
                20                  25                  30

Pro Gly Ala Ser Val Lys Leu Ser Cys Lys Ala Ser Gly Tyr Thr Phe
            35                  40                  45

Thr Thr Tyr Trp Met His Trp Val Lys Gln Arg Pro Gly Gln Gly Leu
        50                  55                  60

Glu Trp Ile Gly Glu Ile Asp Pro Ser Asp Ser Tyr Val Asn Tyr Asn
65                  70                  75                  80

Gln Asn Phe Lys Gly Lys Ala Thr Leu Thr Val Asp Lys Ser Ser Ser
                85                  90                  95

Thr Ala Tyr Ile Gln Leu Ser Ser Leu Thr Ser Glu Asp Ser Ala Val
            100                 105                 110

Tyr Phe Cys Ala Arg Ser Pro Asp Tyr Tyr Gly Thr Ser Leu Ala Trp
        115                 120                 125

Phe Asp Tyr Trp Gly Gln Gly Thr Leu Val Thr Val Ser Thr
        130                 135                 140

<210> SEQ ID NO 15
<211> LENGTH: 396
<212> TYPE: DNA
<213> ORGANISM: Mus musculus

<400> SEQUENCE: 15

```
atgaggtgcc tagctgagtt cctggggctg cttgtgctct ggatccctgg agtcattggg      60
gatattgtga tgactcaggc tgcaccctct gtacctgtca ctcctggaga gtcagtatcc     120
atctcctgca ggtctagtaa gagtcccctg catagtaacg caacattta cttatattgg      180
ttcctgcaga ggccaggcca gtctcctcag ctcctgatat atcggatgtc caaccttgcc    240
tcaggagtcc cagacaggtt cagtggcagt gggtcaggaa ctactttcac actgaaaatc    300
agtagagtgg aggctgagga tgtgggtgtt tattactgta tgcaacatct agaatatccg    360
tacacgttcg gaggggggac caagctggaa ataaaa                               396
```

<210> SEQ ID NO 16
<211> LENGTH: 132
<212> TYPE: PRT
<213> ORGANISM: Mus musculus

<400> SEQUENCE: 16

```
Met Arg Cys Leu Ala Glu Phe Leu Gly Leu Leu Val Leu Trp Ile Pro
1               5                   10                  15
Gly Val Ile Gly Asp Ile Val Met Thr Gln Ala Ala Pro Ser Val Pro
            20                  25                  30
Val Thr Pro Gly Glu Ser Val Ser Ile Ser Cys Arg Ser Ser Lys Ser
        35                  40                  45
Pro Leu His Ser Asn Gly Asn Ile Tyr Leu Tyr Trp Phe Leu Gln Arg
    50                  55                  60
Pro Gly Gln Ser Pro Gln Leu Leu Ile Tyr Arg Met Ser Asn Leu Ala
65                  70                  75                  80
Ser Gly Val Pro Asp Arg Phe Ser Gly Ser Gly Ser Gly Thr Thr Phe
                85                  90                  95
Thr Leu Lys Ile Ser Arg Val Glu Ala Glu Asp Val Gly Val Tyr Tyr
            100                 105                 110
Cys Met Gln His Leu Glu Tyr Pro Tyr Thr Phe Gly Gly Gly Thr Lys
        115                 120                 125
Leu Glu Ile Lys
    130
```

<210> SEQ ID NO 17
<211> LENGTH: 30
<212> TYPE: DNA
<213> ORGANISM: Mus musculus

<400> SEQUENCE: 17

```
ggctacagtt tcaccagcta ctggataaac                                       30
```

<210> SEQ ID NO 18
<211> LENGTH: 51
<212> TYPE: DNA
<213> ORGANISM: Mus musculus

<400> SEQUENCE: 18

```
aatatttatc cttctgatag ttatactaac tacaatcaaa tgttcaagga c              51
```

<210> SEQ ID NO 19
<211> LENGTH: 45
<212> TYPE: DNA
<213> ORGANISM: Mus musculus

<400> SEQUENCE: 19
tggaatcttt cttattactt cgataataac tactacttgg actac           45

<210> SEQ ID NO 20
<211> LENGTH: 48
<212> TYPE: DNA
<213> ORGANISM: Mus musculus

<400> SEQUENCE: 20
aggtctagta agagtctcct gcatagtaat ggcaacactt acttgtat        48

<210> SEQ ID NO 21
<211> LENGTH: 21
<212> TYPE: DNA
<213> ORGANISM: Mus musculus

<400> SEQUENCE: 21
cggatgtcca accttgcctc a                                     21

<210> SEQ ID NO 22
<211> LENGTH: 27
<212> TYPE: DNA
<213> ORGANISM: Mus musculus

<400> SEQUENCE: 22
atgcaacatc tagaatatcc gtggacg                               27

<210> SEQ ID NO 23
<211> LENGTH: 10
<212> TYPE: PRT
<213> ORGANISM: Mus musculus

<400> SEQUENCE: 23

Gly Tyr Ser Phe Thr Ser Tyr Trp Ile Asn
1               5                   10

<210> SEQ ID NO 24
<211> LENGTH: 17
<212> TYPE: PRT
<213> ORGANISM: Mus musculus

<400> SEQUENCE: 24

Asn Ile Tyr Pro Ser Asp Ser Tyr Thr Asn Tyr Asn Gln Met Phe Lys
1               5                   10                  15

Asp

<210> SEQ ID NO 25
<211> LENGTH: 15
<212> TYPE: PRT
<213> ORGANISM: Mus musculus

<400> SEQUENCE: 25

Trp Asn Leu Ser Tyr Tyr Phe Asp Asn Asn Tyr Tyr Leu Asp Tyr
1               5                   10                  15

<210> SEQ ID NO 26
<211> LENGTH: 16
<212> TYPE: PRT
<213> ORGANISM: Mus musculus

<400> SEQUENCE: 26

Arg Ser Ser Lys Ser Leu Leu His Ser Asn Gly Asn Thr Tyr Leu Tyr
1               5                   10                  15

<210> SEQ ID NO 27
<211> LENGTH: 7
<212> TYPE: PRT
<213> ORGANISM: Mus musculus

<400> SEQUENCE: 27

Arg Met Ser Asn Leu Ala Ser
1               5

<210> SEQ ID NO 28
<211> LENGTH: 9
<212> TYPE: PRT
<213> ORGANISM: Mus musculus

<400> SEQUENCE: 28

Met Gln His Leu Glu Tyr Pro Trp Thr
1               5

<210> SEQ ID NO 29
<211> LENGTH: 429
<212> TYPE: DNA
<213> ORGANISM: Mus musculus

<400> SEQUENCE: 29

```
atgggatgga gctgtatcat cctcttcttg gtagcaacag ctacaggtgt ccactcccag    60
gtccaactgc agcagcctgg ggctgagctg gtgaggcctg ggcttcagt gaagctgtcc    120
tgcaaggctt ctggctacag tttcaccagc tactggataa actgggtgaa gcagaggcct   180
ggacaaggcc ttgagtggat cggaaatatt tatccttctg atagttatac taactacaat   240
caaatgttca aggacaaggc cacattgact gtagacaaat cctccaacac agcctacatg   300
cagctcacca gcccgacatc tgaggactct gcggtctatt actgtacaag atggaatctt   360
tcttattact cgataataa ctactacttg gactactggg gccaaggcac cactctcaca   420
gtctcctca                                                          429
```

<210> SEQ ID NO 30
<211> LENGTH: 143
<212> TYPE: PRT
<213> ORGANISM: Mus musculus

<400> SEQUENCE: 30

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Ser Phe
        35                  40                  45

Thr Ser Tyr Trp Ile Asn Trp Val Lys Gln Arg Pro Gly Gln Gly Leu
    50                  55                  60

Glu Trp Ile Gly Asn Ile Tyr Pro Ser Asp Ser Tyr Thr Asn Tyr Asn
65                  70                  75                  80

Gln Met Phe Lys Asp Lys Ala Thr Leu Thr Val Asp Lys Ser Ser Asn
                85                  90                  95

Thr Ala Tyr Met Gln Leu Thr Ser Pro Thr Ser Glu Asp Ser Ala Val
            100                 105                 110

Tyr Tyr Cys Thr Arg Trp Asn Leu Ser Tyr Tyr Phe Asp Asn Asn Tyr
        115                 120                 125

Tyr Leu Asp Tyr Trp Gly Gln Gly Thr Thr Leu Thr Val Ser Ser

<210> SEQ ID NO 31
<211> LENGTH: 396
<212> TYPE: DNA
<213> ORGANISM: Mus musculus

<400> SEQUENCE: 31

```
atgaggtgcc tagctgagtt cctggggctg cttgtgctct ggatccctgg agccattggg    60
gatattgtga tgactcaggc tgcaccctct gtacctgtca ctcctggaga gtcagtatcc   120
atctcctgca ggtctagtaa gagtctcctg catagtaatg gcaacactta cttgtattgg   180
ttcctgcaga ggccaggcca gtctcctcaa ctcctgatat atcggatgtc caaccttgcc   240
tcaggagtcc cagacaggtt cagtggcagt gggtcaggaa ctgctttcac actgagaatc   300
agtagagtgg aggctgagga tgtgggtgtt tattactgta tgcaacatct agaatatccg   360
tggacgttcg gtggaggcac caagctggaa atcaaa                              396
```

<210> SEQ ID NO 32
<211> LENGTH: 132
<212> TYPE: PRT
<213> ORGANISM: Mus musculus

<400> SEQUENCE: 32

Met Arg Cys Leu Ala Glu Phe Leu Gly Leu Leu Val Leu Trp Ile Pro
1               5                   10                  15
Gly Ala Ile Gly Asp Ile Val Met Thr Gln Ala Ala Pro Ser Val Pro
                20                  25                  30
Val Thr Pro Gly Glu Ser Val Ser Ile Ser Cys Arg Ser Ser Lys Ser
            35                  40                  45
Leu Leu His Ser Asn Gly Asn Thr Tyr Leu Tyr Trp Phe Leu Gln Arg
        50                  55                  60
Pro Gly Gln Ser Pro Gln Leu Leu Ile Tyr Arg Met Ser Asn Leu Ala
65                  70                  75                  80
Ser Gly Val Pro Asp Arg Phe Ser Gly Ser Gly Ser Gly Thr Ala Phe
                85                  90                  95
Thr Leu Arg Ile Ser Arg Val Glu Ala Glu Asp Val Gly Val Tyr Tyr
            100                 105                 110
Cys Met Gln His Leu Glu Tyr Pro Trp Thr Phe Gly Gly Gly Thr Lys
        115                 120                 125
Leu Glu Ile Lys
    130